US006972039B2

(12) United States Patent
Metzger et al.

(10) Patent No.: US 6,972,039 B2
(45) Date of Patent: Dec. 6, 2005

(54) FLOATING BEARING KNEE JOINT PROSTHESIS WITH A FIXED TIBIAL POST

(75) Inventors: Robert Metzger, Walkarusa, IN (US); William A. Hartman, Warsaw, IN (US); James M. McKale, Syracuse, IN (US); Jacy C. Hoeppner, Syracuse, IN (US); Kevin A. Haines, Warsaw, IN (US)

(73) Assignee: Biomet, Inc., Warsaw, IN (US)

( * ) Notice: Subject to any disclaimer, the term of this patent is extended or adjusted under 35 U.S.C. 154(b) by 198 days.

(21) Appl. No.: 10/188,305

(22) Filed: Jul. 1, 2002

(65) Prior Publication Data
US 2003/0009232 A1 Jan. 9, 2003

Related U.S. Application Data

(63) Continuation-in-part of application No. 09/695,448, filed on Oct. 24, 2000, now Pat. No. 6,413,279, which is a continuation-in-part of application No. 09/259,873, filed on Mar. 1, 1999, now Pat. No. 6,165,223.

(51) Int. Cl.[7] ............................................... A61F 2/38
(52) U.S. Cl. .................................................. 623/20.29
(58) Field of Search ........................ 623/20.14–20.23, 623/20.27–20.36

(56) References Cited

U.S. PATENT DOCUMENTS

| 3,728,742 | A | 4/1973 | Averill et al. |
| 3,748,662 | A | 7/1973 | Helfet |
| 3,774,244 | A | 11/1973 | Walker |
| 3,958,278 | A | 5/1976 | Lee et al. |
| 3,964,106 | A | 6/1976 | Hutter, Jr. et al. |
| 3,996,624 | A | 12/1976 | Noiles |
| 4,081,866 | A | 4/1978 | Upshaw et al. |
| 4,085,466 | A | 4/1978 | Goodfellow et al. |
| 4,094,017 | A | 6/1978 | Matthews et al. |
| 4,136,405 | A | 1/1979 | Pastrick et al. |
| 4,205,400 | A | 6/1980 | Shen et al. |
| 4,207,627 | A | 6/1980 | Cloutier |
| 4,209,861 | A | 7/1980 | Walker et al. |
| 4,213,209 | A | 7/1980 | Insall et al. |
| 4,215,439 | A | 8/1980 | Gold et al. |
| 4,216,549 | A | 8/1980 | Hillberry et al. |
| 4,219,893 | A | 9/1980 | Noiles |
| 4,224,696 | A | 9/1980 | Murray et al. |
| 4,224,697 | A | 9/1980 | Murray et al. |

(Continued)

FOREIGN PATENT DOCUMENTS

DE 28 02 568 A1 1/1978

(Continued)

OTHER PUBLICATIONS

"AGC, Total Knee System, Intramedullary with Distractor Surgical Technique," brochure, Biomet, Inc. 1989.

(Continued)

Primary Examiner—Eduardo C. Robert
(74) Attorney, Agent, or Firm—Harness, Dickey & Pierce, P.L.C.

(57) ABSTRACT

An articulating bearing knee including a guide post that in a first orientation allows substantially free varus and valgus distraction, but in another constrains the same. The guide post in includes a superior portion that engages a femoral component of a knee prosthesis in a rotated orientation. When the guide post engages the femoral component it may not distract as if it was not engaged. This allows for a control and constraint of such distraction when the knee is rotated and in a weaker position.

14 Claims, 22 Drawing Sheets

U.S. PATENT DOCUMENTS

| | | |
|---|---|---|
| 4,242,759 A | 1/1981 | White |
| 4,249,270 A | 2/1981 | Bahler et al. |
| 4,257,129 A | 3/1981 | Volz |
| 4,285,070 A | 8/1981 | Averill |
| 4,298,992 A | 11/1981 | Burstein et al. |
| 4,301,553 A | 11/1981 | Noiles |
| 4,309,778 A | 1/1982 | Buechel et al. |
| 4,340,978 A | 7/1982 | Buechel et al. |
| 4,462,120 A | 7/1984 | Rambert et al. |
| 4,470,158 A | 9/1984 | Pappas et al. |
| 4,538,305 A | 9/1985 | Engelbrecht et al. |
| 4,568,348 A | 2/1986 | Johnson et al. |
| 4,586,933 A | 5/1986 | Shoji et al. |
| 4,634,444 A | 1/1987 | Noiles |
| 4,637,382 A | 1/1987 | Walker |
| 4,673,407 A | 6/1987 | Martin |
| 4,711,639 A | 12/1987 | Grundei |
| 4,714,474 A | 12/1987 | Brooks, Jr. et al. |
| 4,728,332 A | 3/1988 | Albrektsson |
| 4,808,185 A | 2/1989 | Penenberg et al. |
| 4,822,362 A | 4/1989 | Walker et al. |
| 4,822,365 A | 4/1989 | Walker et al. |
| 4,865,607 A | 9/1989 | Witzel et al. |
| 4,883,488 A | 11/1989 | Bloebaum et al. |
| 4,888,021 A | 12/1989 | Forte et al. |
| 4,892,547 A | 1/1990 | Brown |
| 4,911,721 A | 3/1990 | Branemark et al. |
| 4,950,297 A | 8/1990 | Elloy et al. |
| 4,950,298 A | 8/1990 | Gustilo et al. |
| 4,959,071 A | 9/1990 | Brown et al. |
| 4,997,445 A | 3/1991 | Hodorek |
| 5,007,933 A | 4/1991 | Sidebotham et al. |
| 5,011,496 A | 4/1991 | Forte et al. |
| 5,037,439 A | 8/1991 | Albrektsson et al. |
| 5,047,057 A | 9/1991 | Lawes |
| 5,064,437 A | 11/1991 | Stock et al. |
| 5,071,438 A | 12/1991 | Jones et al. |
| 5,080,675 A | 1/1992 | Lawes et al. |
| 5,092,895 A | 3/1992 | Albrektsson et al. |
| 5,116,375 A | 5/1992 | Hofmann |
| 5,116,376 A | 5/1992 | May |
| 5,133,758 A | 7/1992 | Hollister |
| 5,147,405 A | 9/1992 | Van Zile et al. |
| 5,147,406 A | 9/1992 | Houston et al. |
| 5,171,283 A | 12/1992 | Pappas et al. |
| 5,176,710 A | 1/1993 | Hahn et al. |
| 5,181,925 A | 1/1993 | Houston et al. |
| 5,197,987 A | 3/1993 | Koch et al. |
| 5,201,881 A | 4/1993 | Evans |
| 5,219,362 A | 6/1993 | Tuke et al. |
| 5,226,916 A | 7/1993 | Goodfellow et al. |
| 5,236,461 A * | 8/1993 | Forte ................. 623/20.27 |
| 5,271,747 A | 12/1993 | Wagner et al. |
| 5,282,868 A | 2/1994 | Bahler |
| 5,282,870 A | 2/1994 | Moser et al. |
| 5,314,482 A | 5/1994 | Goodfellow et al. |
| 5,314,483 A | 5/1994 | Wehrli et al. |
| 5,330,532 A | 7/1994 | Ranawat |
| 5,330,533 A | 7/1994 | Walker |
| 5,330,534 A | 7/1994 | Herrington et al. |
| 5,358,527 A | 10/1994 | Forte |
| 5,358,529 A | 10/1994 | Davidson |
| 5,358,530 A | 10/1994 | Hodorek |
| 5,358,531 A | 10/1994 | Goodfellow et al. |
| 5,370,699 A | 12/1994 | Hood et al. |
| 5,370,700 A | 12/1994 | Sarkisian et al. |
| 5,370,701 A | 12/1994 | Finn |
| 5,387,240 A | 2/1995 | Pottenger et al. |
| 5,395,401 A | 3/1995 | Bahler |
| 5,405,394 A | 4/1995 | Davidson |
| 5,405,395 A | 4/1995 | Coates |
| 5,405,396 A | 4/1995 | Heldreth et al. |
| 5,413,604 A | 5/1995 | Hodge |
| 5,413,608 A | 5/1995 | Keller |
| 5,466,530 A | 11/1995 | England et al. |
| 5,480,446 A | 1/1996 | Goodfellow et al. |
| 5,514,183 A | 5/1996 | Epstein et al. |
| 5,549,686 A | 8/1996 | Johnson et al. |
| 5,549,689 A | 8/1996 | Epstein et al. |
| 5,549,690 A | 8/1996 | Hollister et al. |
| 5,556,432 A | 9/1996 | Kubein-Meesenburg et al. |
| 5,571,197 A | 11/1996 | Insall |
| 5,609,639 A | 3/1997 | Walker |
| 5,609,643 A | 3/1997 | Colleran et al. |
| 5,609,645 A | 3/1997 | Vinciguerra |
| 5,639,279 A | 6/1997 | Burkinshaw et al. |
| 5,641,323 A | 6/1997 | Caldarise |
| 5,658,342 A | 8/1997 | Draganich et al. |
| 5,658,344 A | 8/1997 | Hurlburt |
| 5,662,158 A | 9/1997 | Caldarise |
| 5,683,467 A | 11/1997 | Pappas |
| 5,683,468 A | 11/1997 | Pappas |
| 5,702,458 A | 12/1997 | Burstein et al. |
| 5,702,466 A | 12/1997 | Pappas et al. |
| 5,725,584 A | 3/1998 | Walker et al. |
| 5,755,801 A | 5/1998 | Walker et al. |
| 5,755,802 A | 5/1998 | Gerber |
| 5,800,552 A | 9/1998 | Forte |
| 5,824,096 A | 10/1998 | Pappas et al. |
| 5,824,100 A | 10/1998 | Kester et al. |
| 5,824,102 A | 10/1998 | Buscayret |
| 5,824,103 A | 10/1998 | Williams |
| 5,871,542 A | 2/1999 | Goodfellow et al. |
| 5,871,545 A | 2/1999 | Goodfellow et al. |
| 5,871,546 A | 2/1999 | Colleran et al. |
| 5,879,387 A | 3/1999 | Jones et al. |
| 5,879,392 A | 3/1999 | McMinn |
| 5,879,394 A | 3/1999 | Ashby et al. |
| 5,906,643 A | 5/1999 | Walker |
| 5,997,577 A | 12/1999 | Herrington et al. |
| 6,004,352 A | 12/1999 | Buni |
| 6,039,764 A | 3/2000 | Pottenger et al. |
| 6,068,658 A | 5/2000 | Insall et al. |
| 6,080,195 A | 6/2000 | Colleran et al. |
| 6,090,144 A | 7/2000 | Letot et al. |
| 6,099,570 A | 8/2000 | Livet et al. |
| 6,117,175 A | 9/2000 | Bosredon |
| 6,123,729 A | 9/2000 | Insall et al. |
| 6,152,960 A | 11/2000 | Pappas |
| 6,162,254 A | 12/2000 | Timoteo |
| 6,165,223 A | 12/2000 | Metzger et al. |
| 6,203,576 B1 | 3/2001 | Afriat et al. |
| 6,210,444 B1 | 4/2001 | Webster et al. |
| 6,210,445 B1 | 4/2001 | Zawadzki |
| 6,217,618 B1 | 4/2001 | Hileman |
| 6,485,519 B2 * | 11/2002 | Meyers et al. ............ 623/20.24 |

FOREIGN PATENT DOCUMENTS

| | | |
|---|---|---|
| DE | 35 29 894 A1 | 3/1987 |
| DE | 40 09 360 A1 | 8/1991 |
| EP | 0 186 471 A3 | 7/1986 |
| EP | 0 327 297 A2 | 8/1989 |
| EP | 0 346 183 A1 | 12/1989 |
| EP | 0 349 173 A1 | 1/1990 |
| EP | 0 381 352 A1 | 8/1990 |
| EP | 0 442 330 A2 | 8/1991 |
| EP | 0 519 873 A2 | 6/1992 |
| EP | 0 498 586 A1 | 8/1992 |
| EP | 0 510 178 B1 | 10/1992 |
| EP | 0 510 299 A1 | 10/1992 |
| EP | 0 627 203 A2 | 12/1994 |
| EP | 0 592 750 B1 | 1/1999 |
| EP | 0 970 667 A | 1/2000 |

| | | |
|---|---|---|
| EP | 653 927 B1 | 3/2001 |
| FR | 2663-536 A | 6/1990 |
| FR | 2 685 632 | 12/1991 |
| FR | 2 758 456 A | 7/1998 |
| GB | 1 534 263 | 11/1978 |
| GB | 2 219 942 A | 12/1989 |
| GB | 2 296 443 A | 7/1996 |
| GB | 2313314 | 4/2000 |
| WO | WO 92/03108 | 3/1992 |
| WO | WO 92/08424 | 12/1992 |
| WO | WO 94/26212 | 11/1994 |
| WO | WO 96/03097 | 2/1996 |
| WO | WO 96/24311 | 8/1996 |
| WO | WO 98/02116 | 1/1998 |

OTHER PUBLICATIONS

"AGC, Total Knee System, Intramedullary with Distractor Surgical Overview," brochure, Biomet, Inc. 1989.

"AGC, Total Knee System, Unicondylar Surgical Overview," brochure, Biomet, Inc. 1989.

"AGC, Total Knee System, Surgical Overview featuring Accu-Line TM Knee Instrumentation," brochure, Biomet, Inc., copyright 1991.

"Controlling the Motion of Total Knee Replacements using Intercondylar Guide Surfaces," Journal of Orthopedic Research, Walker, P. and Sathasivam, S., 2000, pp. 48, 54.

"Stability and Range of Motion of Insall-Burstein Condylar Prostheses", The Journal of Arthroplasty, vol. 10, No. 3 1995, Kocmond, J., Delp, S. and Stern, S., pp. 383, 386.

"The Transepicondylar Axis Approximates the Optimal Flexion Axis of the Knee," Clinical Orthopaedics and Related Research, No. 356, Nov. 1998, Churchill, D., Incavo, S., Johnson, C. and Beynnon, B., pp. 111, 117.

"AGC, Total Knee System, Tradition Series," brochure, Biomet, Inc. copyright 1995.

"Interaction Between Active and Passive Knee Stabilizers During Level Walking," O.D. Schipplein and T.P. Andriacchi, Journal of Orthopaedic Research, 1991.

"Maxim, The Complete Knee System," brochure, Biomet, Inc., copyright 1995.

"Performance The Total Knee System," brochure, Biomet, Inc., copyright 1997.

"The Role of Joint Load in Knee Stability," Keith L. Markolf, PhD., William L. Bargar, M.D., Stephen C. Shoemaker, B.S. and Harlan C. Amstutz, M.D., Journal of Bone and Joint Surgery, Incorporated, copyright 1981.

"Trac Knee System" Design Rationale, Louis F. Daraganich, PhD., Lawrency A. Pottenger, M.D., PHD., Nov. 1996.

Aglietti, P., Buzzi, R., and Menchetti, P.P.M., "Total Knee Replacement—Problems Related to the Posterior Cruciate Ligament and Fixed Versus Mobile Bearings,"0 European Federation of National Associations of Orthopaedics and Traumatology, pp. 15-24, undated (1996 or later).

H. Kurosawa, et al., "Geometry and Motion of the Knee for Implant and Orthotic Design," J. Biomechanics, vol. 18, No. 7, pp. 287-499 (1985).

Menchetti, Paolo, M., M.D., Walker, Peter, S. PhD. "Mechanical Evaluation of Mobile Bearing Knees," the American Journal of Knee Surgery, vol. 10, No. 2, Spring 1997, pp. 73-82.

"The Profix Total Knee System," by Smith & Nephew, copyright 1999, 2 sheets.

* cited by examiner

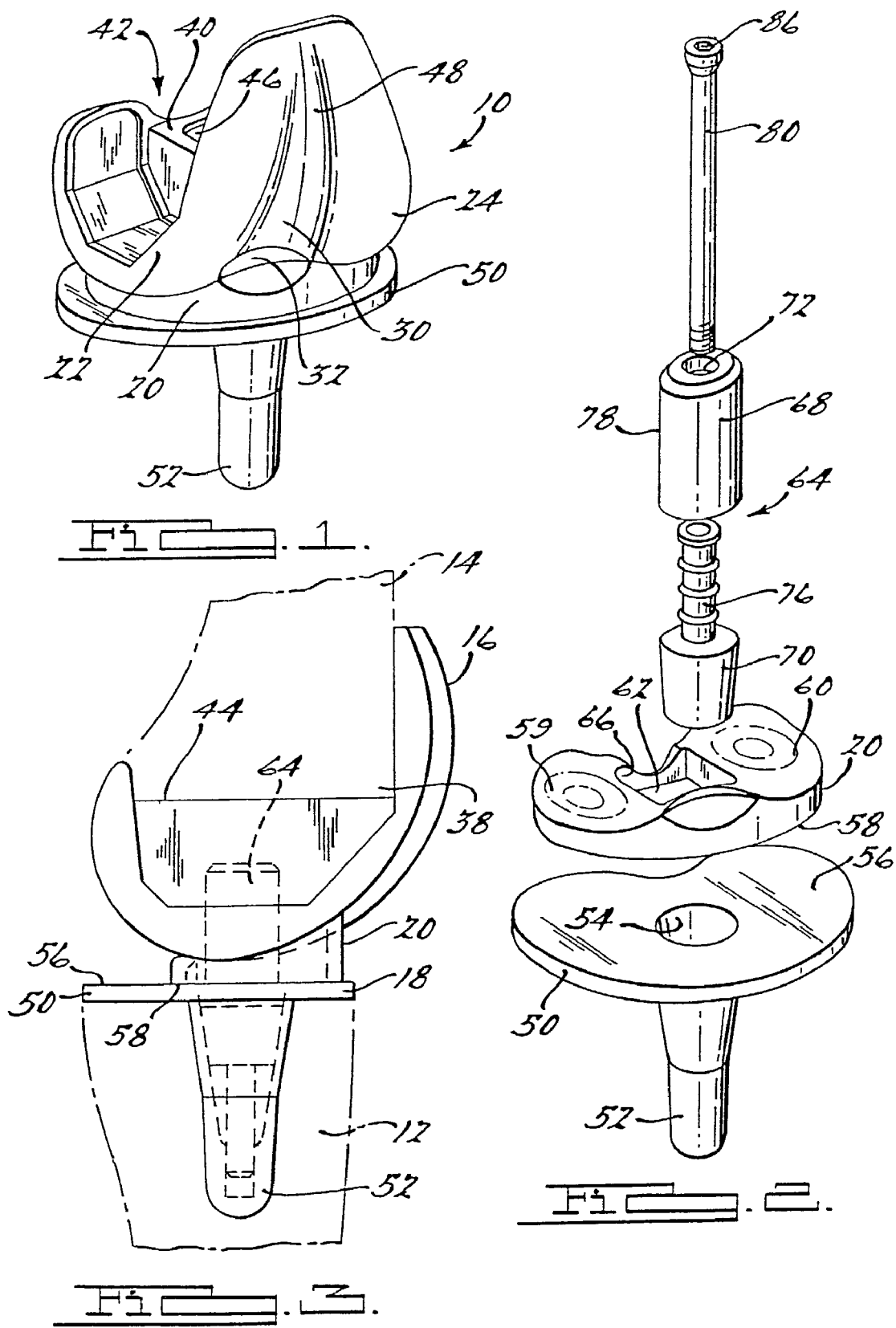

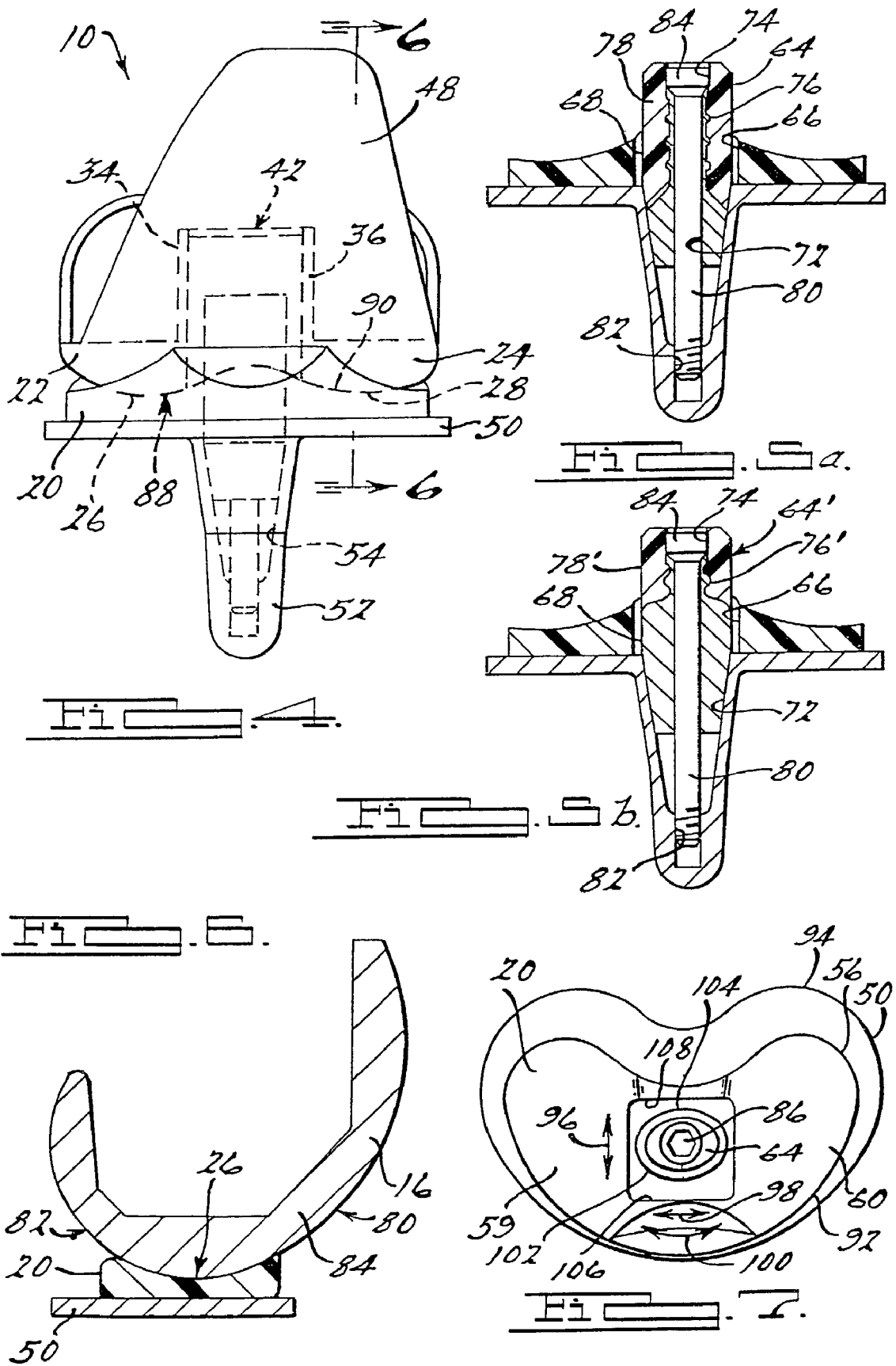

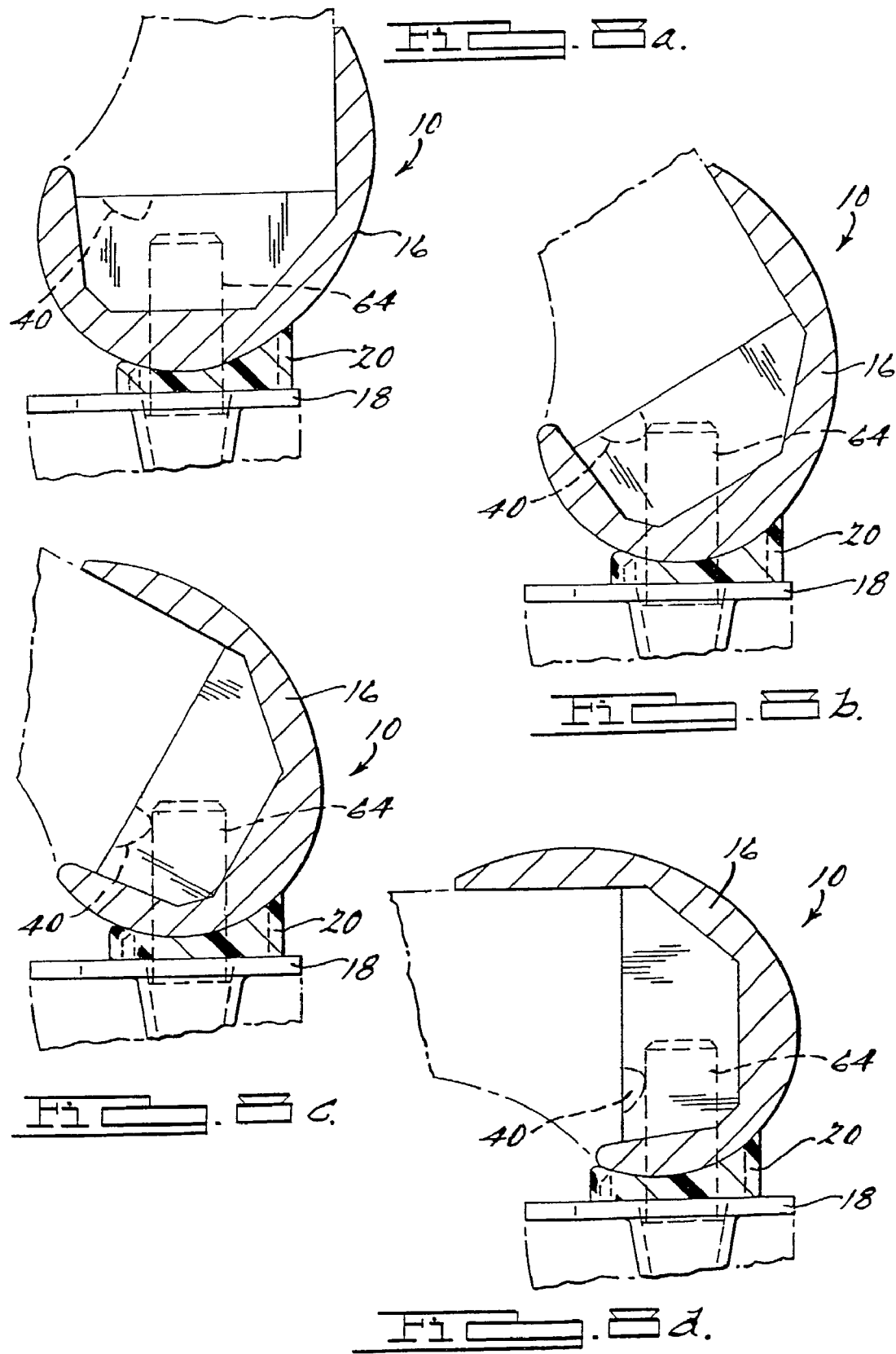

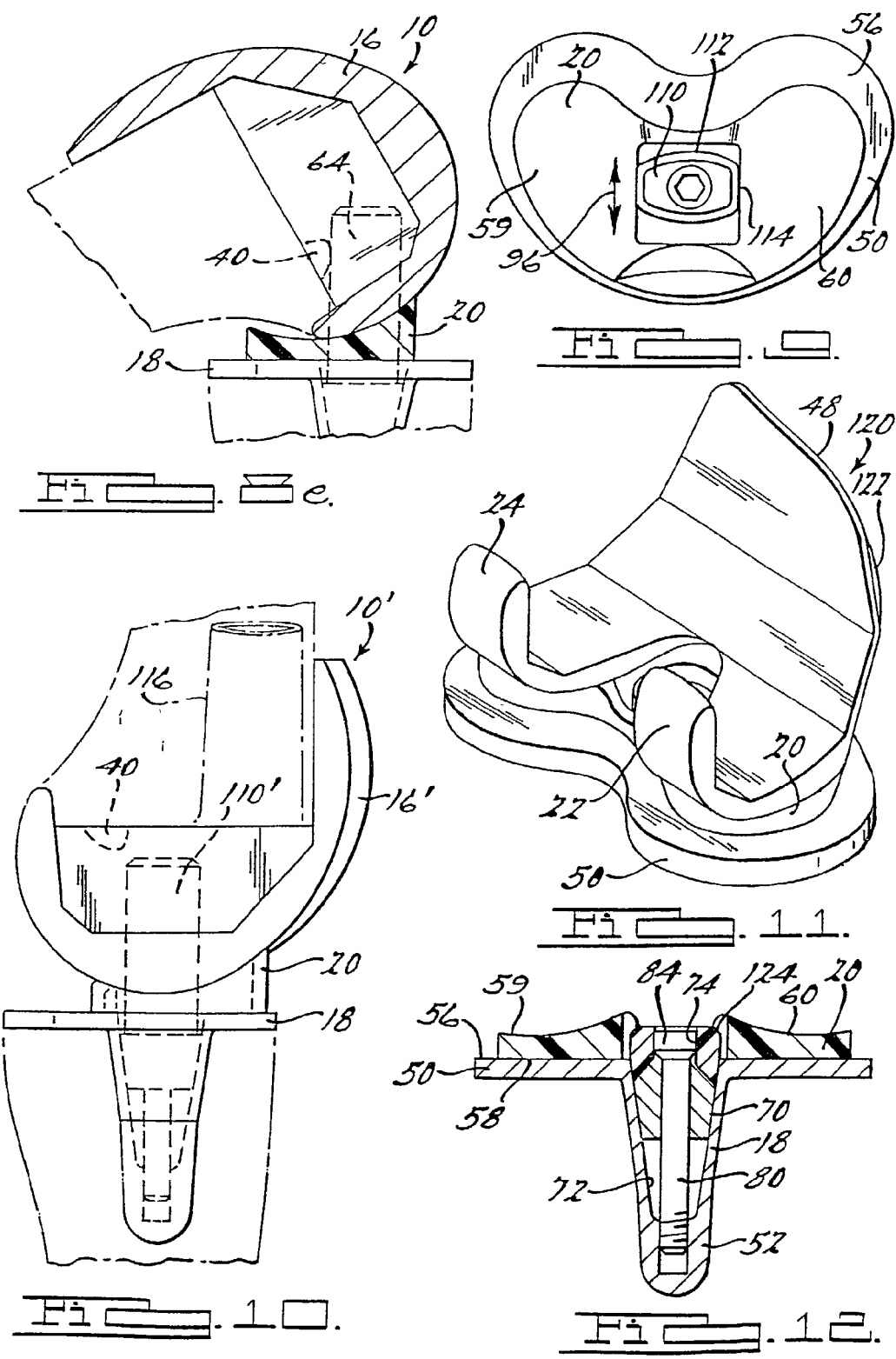

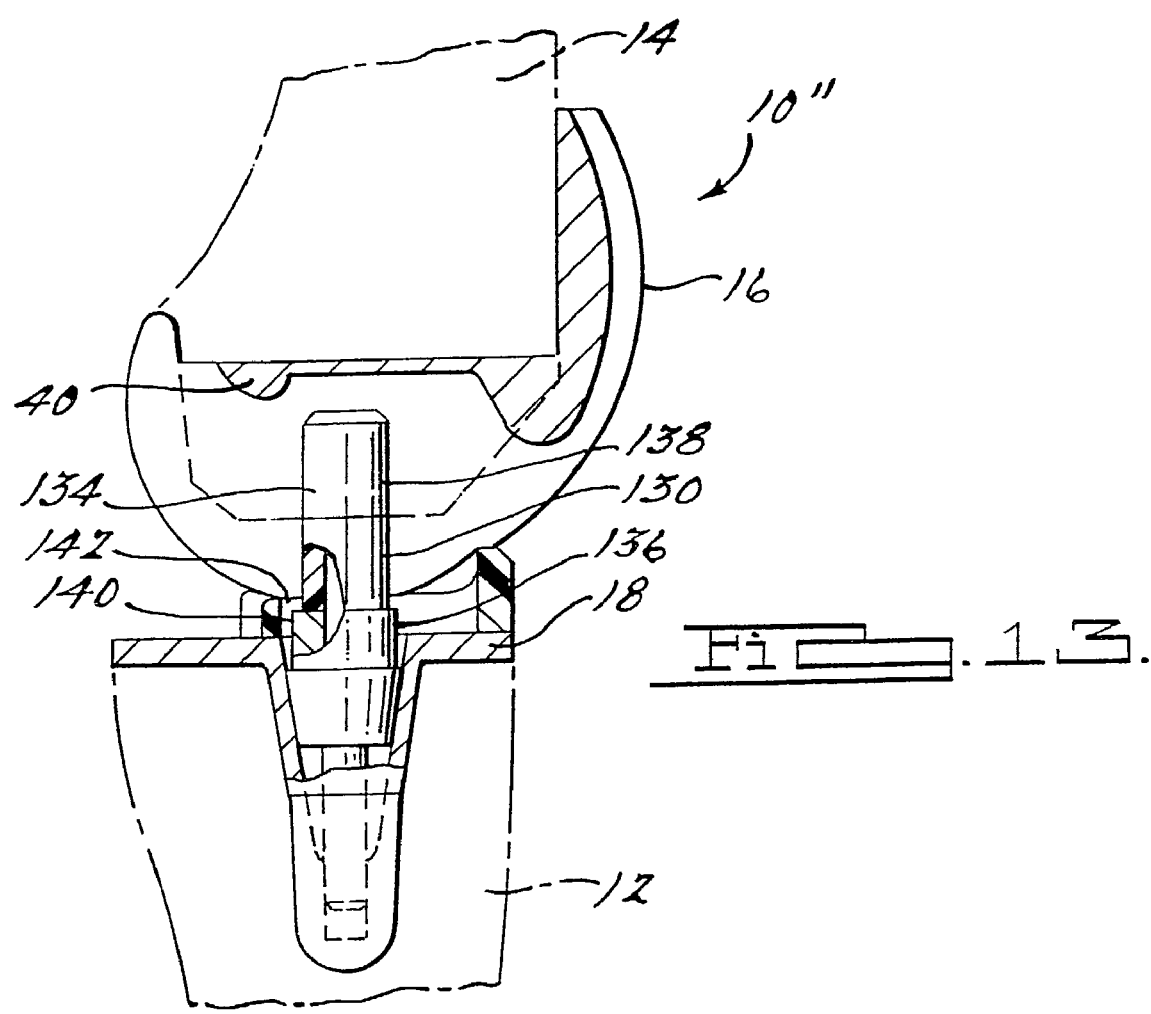

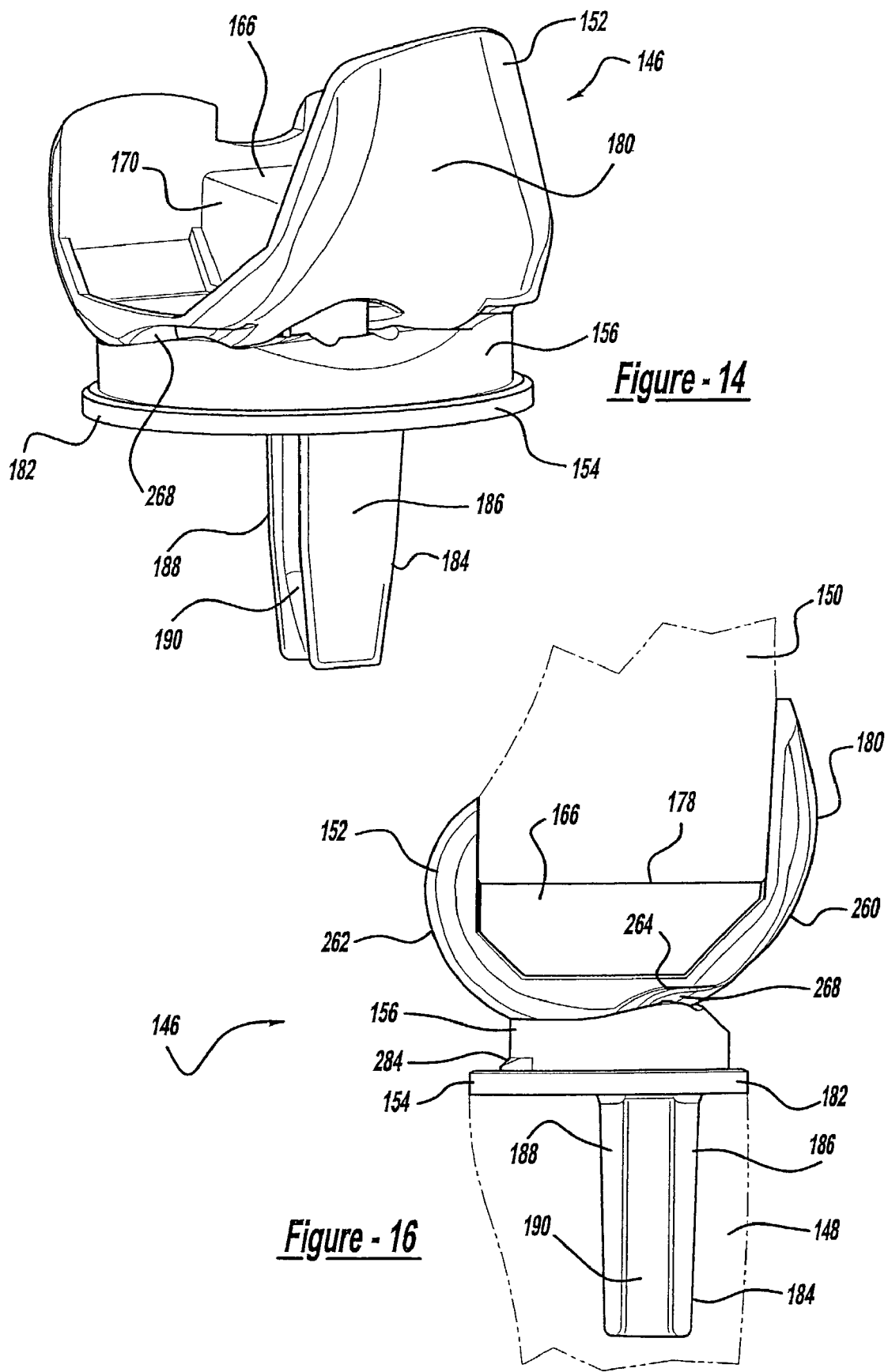

FLOATING BEARING KNEE JOINT PROSTHESIS WITH A FIXED TIBIAL POST

CROSS-REFERENCE TO RELATED APPLICATION

This is a continuation-in-part application of U.S. patent application Ser. No. 09/695,448, filed Oct. 24, 2000, entitled "Floating Bearing Knee Joint Prosthesis With a Fixed Tibial Post," now U.S. Pat No. 6,413,279; which is a continuation-in-part of U.S. patent application Ser. No. 09/259,873, filed Mar. 1, 1999, entitled "Floating Bearing Knee Joint Prosthesis With A Fixed Tibial Post, now U.S. Pat. No. 6,165,223 issued Dec. 26, 2000.

BACKGROUND

This invention relates generally to a knee joint prosthesis which replaces the articulating knee portion of the femur and tibia, and more particularly, to a floating bearing knee joint prosthesis having a fixed tibial post.

A knee joint prosthesis typically comprises a femoral component and a tibial component. The femoral component and the tibial component are designed to be surgically attached to the distal end of the femur and the proximal end of the tibia, respectively. The femoral component is further designed to cooperate with the tibial component in simulating and articulating motion of an anatomical knee joint.

Motion of a natural knee is kinematically complex. During a relatively broad range of flexion and extension, the articular or bearing surfaces of a natural knee experience rotation, medial and lateral angulation, translation in the sagittal plane, rollback and sliding. Knee joint prostheses, in combination with ligaments and muscles, attempt to duplicate this natural knee motion, as well as absorb and control forces generated during the range of flexion. Depending on the degree of damage or deterioration of the knee tendons and ligaments, however, it may be necessary for a knee joint prosthesis to eliminate one or more of these motions in order to provide adequate stability.

Many knee prosthetics include guide posts or posterior stabilized posts that limit and control the movement of the prosthetic knee joint. Most often, however, these guide posts provide the same limitation of motion regardless of the rotation of the knee. Specifically, it is not generally known to provide a knee prosthetic including a guide post that varies the varus or valgus distraction of the knee depending upon the rotation of the knee. Therefore, it is desirable to provide a knee joint prosthesis wherein the amount of varus and valgus distraction may be altered depending upon the rotation of the knee.

SUMMARY

A knee prosthetic including a guide post for constraining varus and valgus distraction. The knee prosthetic including a tibial component with the guide post to variably control the degree of varus or valgus distraction of the knee prosthetic. The guide post of the knee prosthetic allows a predetermined varus or valgus distraction at a first degree of rotation or first position and a second predetermined varus or valgus distraction at a second degree of rotation or second position.

An alternative embodiment includes a prosthesis for replacing a knee joint between a femur and a tibia. The prosthesis includes a femoral component having a first condylar portion and a second condylar portion with an inter-condylar box, including a first side wall spaced apart from a second side wall, disposed between said first condylar portion and said second condylar portion. A tibial component is adapted to be implanted into the tibia with a guide post extending superiorly from said tibial component. The guidepost includes a median plane dimension or a coronal plane dimension greater than the other dimension. The guide post is further adapted to extend into the inter-condylar box when the prosthesis is implanted in the knee joint. The femoral component is adapted to rotate about the guidepost between a first position and a second position. A varus distraction or valgus distraction is limited when the femoral component is in the second position.

Another embodiment of the prosthesis for replacement of a knee joint between a femur and a tibia includes a femoral component with a first condylar portion and a second condylar portion spaced apart. An inter-condylar box is defined between the first condylar portion and the second condylar portion and includes a first side wall extending superiorly from the first condylar portion and a second side wall extending superiorly from the second condylar portion. A guide post operably engages the inter-condylar box. The femoral component is adapted to be positioned between an engaged and a non-engaged position such that when the femoral component is in the engaged position the femoral component has substantially limited varus distraction or valgus distraction.

Yet, another embodiment of a prosthesis for replacement of a knee joint between a femur and a tibia includes a femoral component having a first condylar portion and a second condylar portion spaced apart. Furthermore, the femoral component includes an inter-condylar box, defined between the first condylar portion and the second condylar portion, including a first side wall extending superiorly of the first condylar portion and a second side wall extending superiorly of the second condylar portion. A guide post extends into the inter-condylar box. The femoral component is operable to be displaced between a first position and a second position, such that the guide post engages the inter-condylar box when the femoral component is in the second position. When the femoral component is in the second position the femoral component includes substantially limited varus distraction or valgus distraction.

Another embodiment of a prosthesis for replacing the knee joint between a femur and a tibia includes a femoral component including a first condylar portion and a second condylar portion with an inter-condylar box, including a first side wall spaced apart from a second side wall, disposed between said first condylar portion and said second condylar portion. A tibial component, adapted to be implanted into the tibia has a guide post extending superiorly from the tibial component, wherein the guidepost includes a sagittal plane taper to a superior end of the guidepost. The guide post is adapted to extend into the inter-condylar box when the prosthesis is implanted in the knee joint. The femoral component is adapted to rotate about the guidepost between a first position and a second position. The varus distraction or valgus distraction, of the prosthesis, is limited when the femoral component is in the second position.

Further areas of applicability of the present invention will become apparent from the detailed description provided hereinafter. It should be understood that the detailed description and specific examples, while indicating the preferred embodiment of the invention, are intended for purposes of illustration and are not intended to limit the scope of the invention.

BRIEF DESCRIPTION OF THE DRAWINGS

Still other advantages of the present invention will become apparent to those skilled in the art after reading the following specification and by reference to the drawings in which:

FIG. 1 is a perspective view of a posterior stabilized (PS) knee joint prosthesis according to the teachings of a first preferred embodiment of the present invention;

FIG. 2 is an exploded perspective view of a tibial component and bearing element of the posterior stabilized (PS) knee joint prosthesis of FIG. 1;

FIG. 3 is a sagittal elevational view of the posterior stabilized (PS) knee joint prosthesis shown in FIG. 1 with a tibia and a femur of the natural knee shown in phantom;

FIG. 4 is a coronal elevational view of the posterior stabilized (PS) knee joint prosthesis shown in FIG. 1;

FIG. 5a is a coronal sectional view of the tibial component and bearing member of the posterior stabilized (PS) knee joint prosthesis of FIG. 3;

FIG. 5b is a coronal sectional view of the tibial component and bearing member of the posterior stabilized (PS) knee joint prosthesis of FIG. 3 according to the teaching of a second preferred embodiment of the present invention;

FIG. 6 is a sagittal sectional view of the posterior stabilized (PS) knee joint prosthesis taken through line 6—6 of FIG. 4;

FIG. 7 is a top view of the assembled tibial component and bearing member of FIG. 1;

FIGS. 8a–8e are partial sagittal sectional views of the posterior stabilized (PS) knee joint prosthesis shown in FIG. 1 illustrating five different positions of the femoral component with respect to the tibial component during a range of flexion from full extension to full flexion;

FIG. 9 is a top view of an assembled tibial component and bearing component of a fully constrained knee joint prosthesis according to the teachings of a second preferred embodiment of the present invention;

FIG. 10 is a sagittal elevational view of the fully constrained knee joint prosthesis of FIG. 9 with the tibia and the femur of the natural knee shown in phantom;

FIG. 11 is a perspective view of a primary knee joint prosthesis according to the teachings of a third preferred embodiment of the present invention;

FIG. 12 is a coronal sectional view of the tibial component and bearing member of the primary knee joint prosthesis of FIG. 11;

FIG. 13 is a partial sagittal sectional view of a posterior stabilized (PS) knee joint prosthesis according to the teachings of a fourth preferred embodiment of the present invention;

FIG. 14 is a perspective view of a posterior stabilized (PS) knee joint prosthesis according to the teachings of a fifth preferred embodiment of the present invention;

FIG. 16 is a sagittal elevational view of the posterior stabilized (PS) knee joint prosthesis, shown in FIG. 14 with a tibia and a femur of the natural knee shown in phantom;

DETAILED DESCRIPTION OF THE EMBODIMENTS

Figure 15:
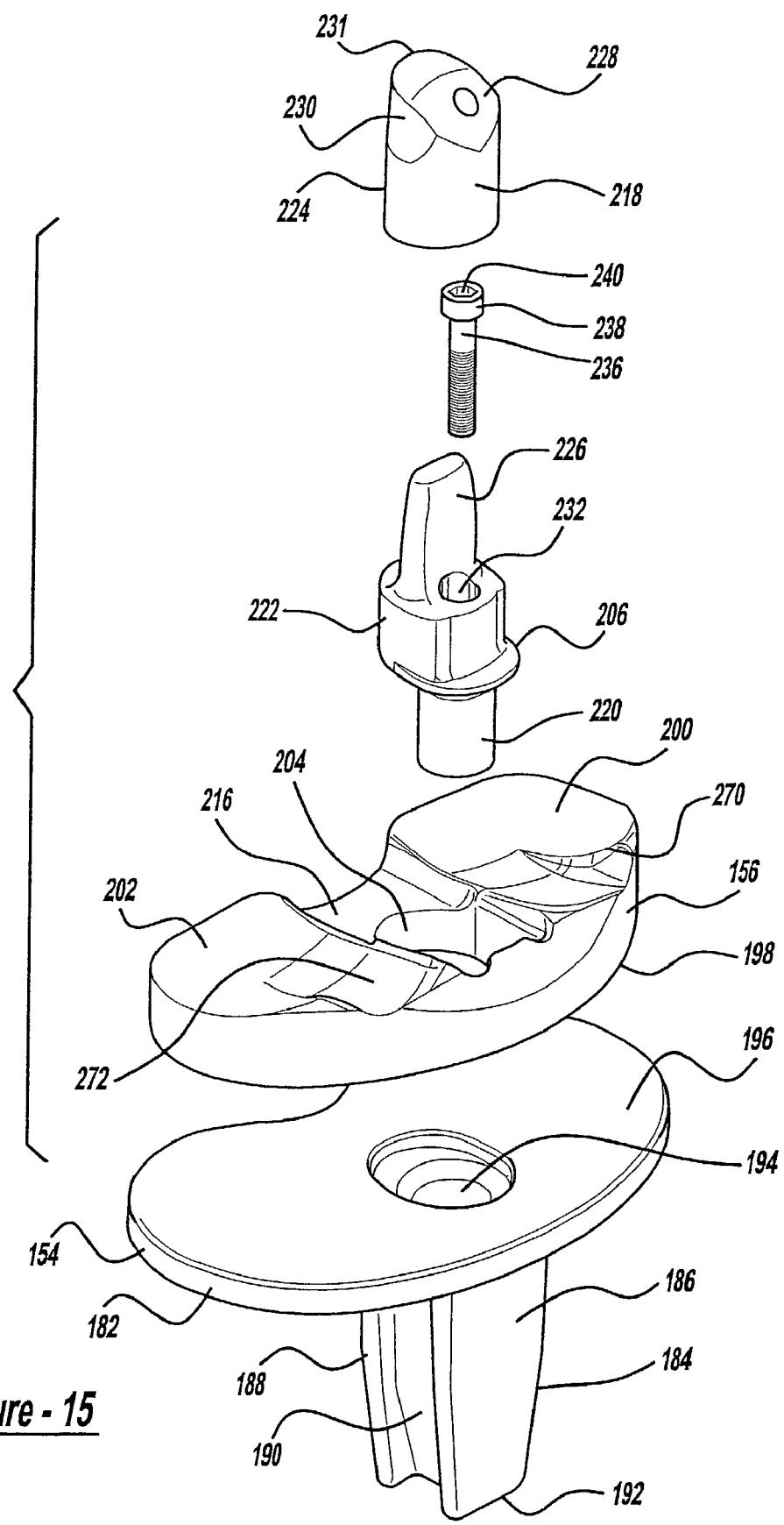
FIG. 15 is an exploded perspective view of a tibial component and bearing element of the posterior stabilized (PS) knee joint prosthesis of FIG. 14.
Figure 17:
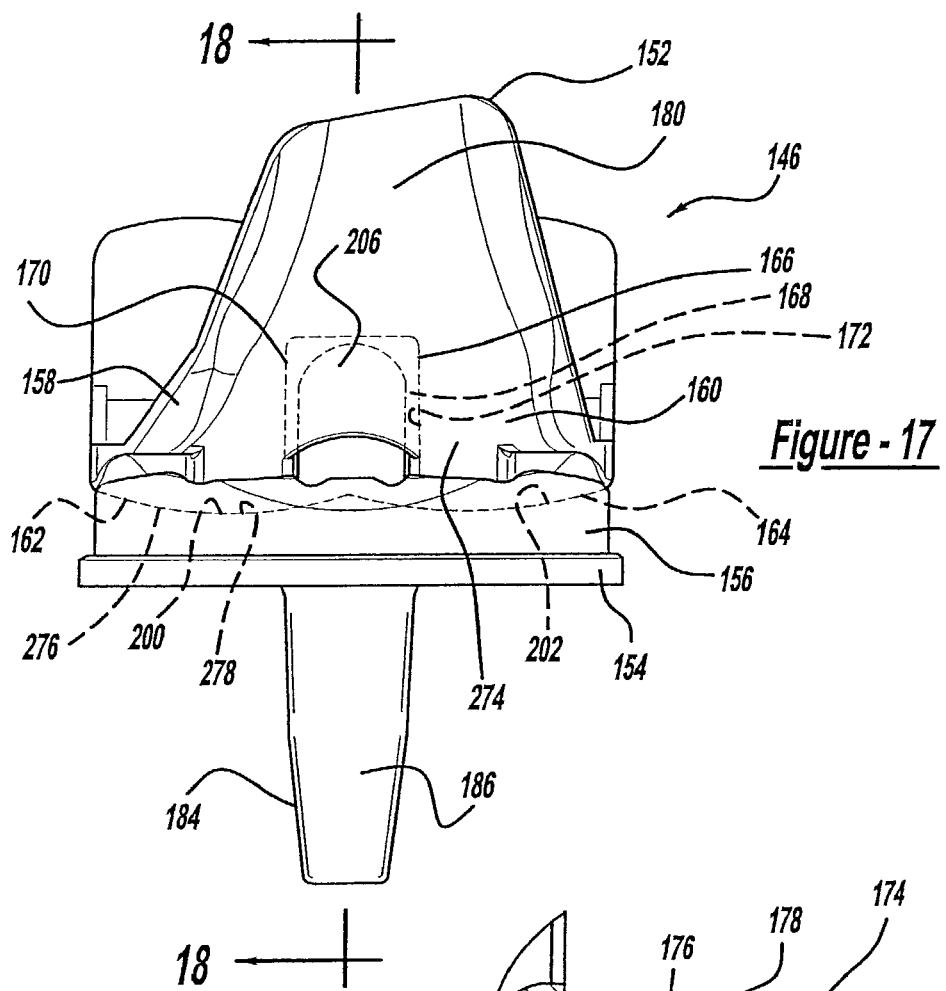
FIG. 17 is a coronal elevational view of the posterior stabilized (PS) knee joint prosthesis shown in FIG. 14.
Figure 18:
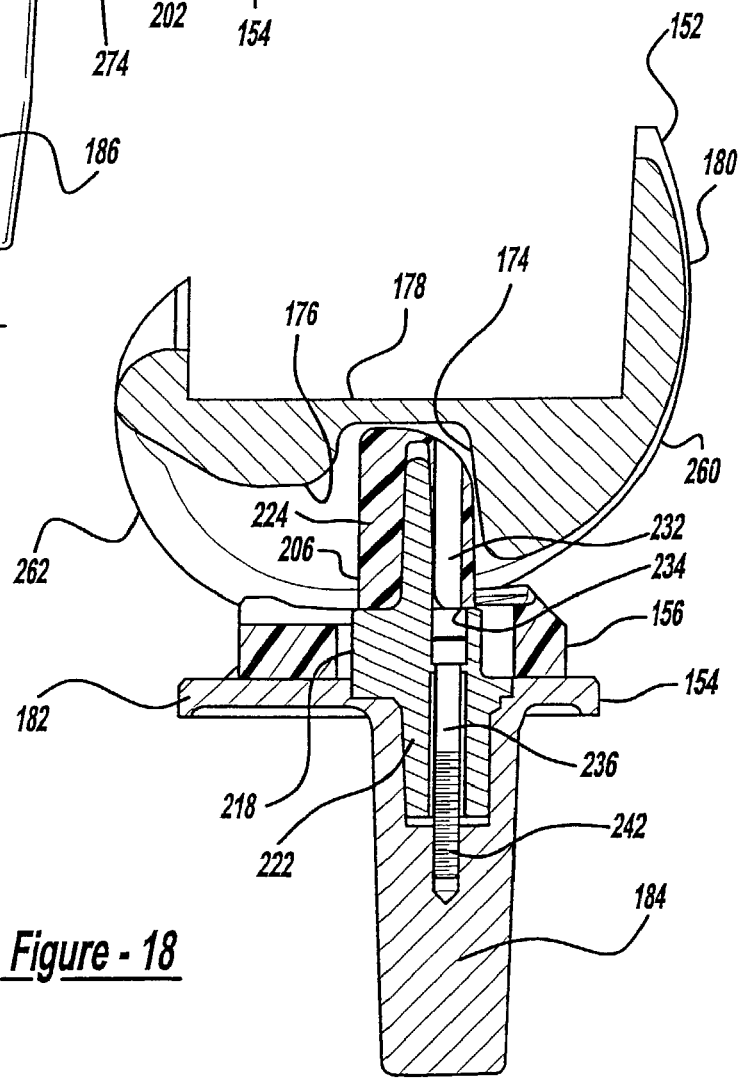
FIG. 18 is a sagittal sectional view of the posterior stabilized (PS) knee joint prosthesis of FIG. 14 taken about line 18—18 of FIG. 17.
Figure 19:
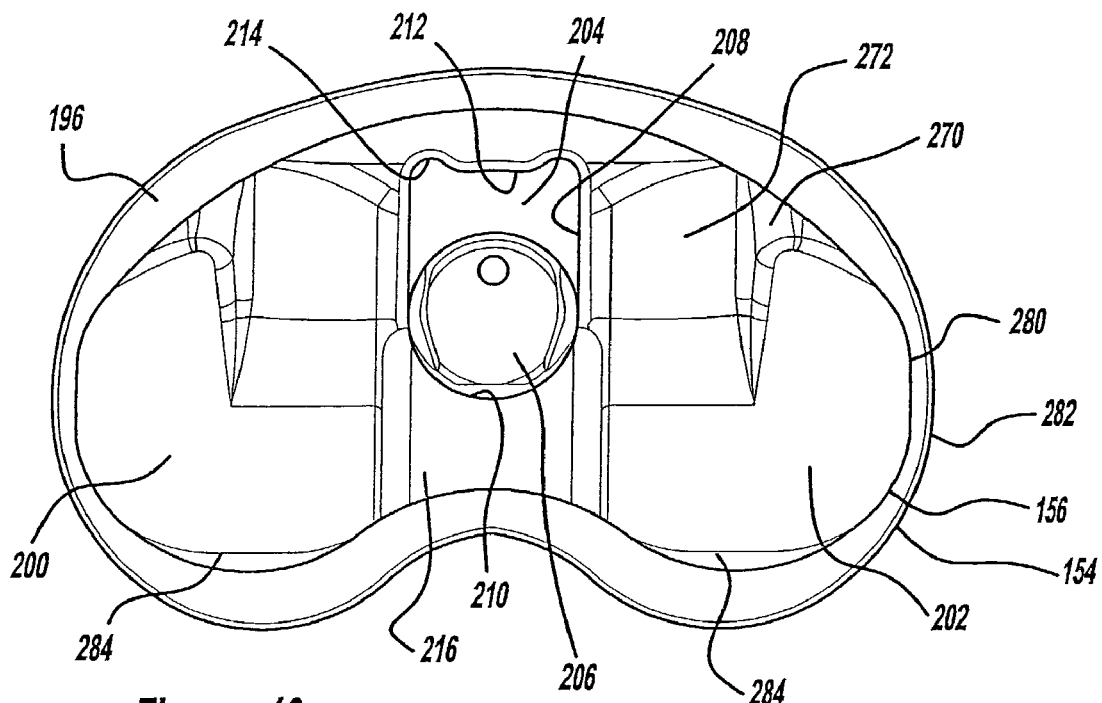
FIG. 19 is a top view of the assembled tibial component and bearing member of the posterior stabilized (PS) knee joint prosthesis of FIG. 14.

The following description of the embodiments concerning a floating bearing knee joint prosthesis with a fixed modular tibial post are merely exemplary in nature and are not intended to limit the invention or its application or uses. Moreover, while the present invention is described in detail below generally with respect to a posterior stabilized (PS) knee joint prosthesis, it will be appreciated by those skilled in the art that the present invention is clearly not limited to only a posterior stabilized (PS) knee joint prosthesis and may be applied to various other types of knee joint prosthesis such as a primary knee joint prosthesis and a fully constrained knee joint prosthesis, as further discussed herein.

Referring to FIGS. 1–4, there is shown a knee joint prosthesis 10 according to the teachings of a first preferred embodiment of the present invention. The knee joint prosthesis 10 is generally known as a posterior stabilized (PS) knee joint prosthesis 10 which is designed to provide adequate stability in case of moderate deterioration or instability of the human knee. This most typically occurs when the anterior and posterior cruciate ligaments are sacrificed or dysfunctional and the medial and lateral collateral ligaments remain functionally intact. The knee joint prosthesis 10 is shown in FIGS. 3 and 4 as being secured to a tibia 12 and a femur 14 of a surgically resected left knee joint, with the tibia 12 and the femur 14 shown in phantom, and with the understanding that a suitable right knee joint prosthesis can be similarly constructed. The knee joint prosthesis 10 includes a femoral component 16, a tibial component 18 and a floating tibial bearing 20.

The femoral component 16 is adapted to be secured to a distal end of the femur 14 and includes a first condylar portion 22 and a second condylar portion 24 that provide a first femoral bearing surface 26 and a second femoral bearing surface 28, respectively. The first and second condylar portions 22 and 24 of the femoral component 16 are interconnected by an intercondylar portion 30 that defines an intercondylar recess 32. The intercondylar portion 30 includes a first lateral sidewall 34 and a second lateral sidewall 36 that are substantially planar and parallel to one another. The anterior portions of the first and second lateral sidewalls 34 and 36 are connected by an anterior wall 38 and the posterior portions of the first and second lateral sidewalls 34 and 36 are connected by a posterior engagement member or elongated cam 40. The intercondylar portion 30 which includes the first and second lateral sidewalls 34 and 36, the anterior wall 38 and the posterior engagement member 40 define the perimeter of a box 42 that defines the intercondylar recess 32.

Positioned atop the box 42 is a substantially planar integral top 44 that defines an elongated opening or bore 46. A closed box may also be utilized in place of the open box 42. The femoral component 16 further includes an arcuate patellar portion 48 which is disposed on the anterior surface of the femoral component 16. The patellar portion 48 is shaped to allow anatomical tracking of a natural or prosthetic patella. The patella prostheses which are compatible with the present invention may be of varying shape, such as round or dome shaped and may be constructed from polyethylene, polyethylene with metal backing or other suitable materials. The femoral component 16 including the box 42 is preferably formed as a unitary structure and preferably cast of a biocompatible high strength alloy, such as a cobalt-chromium-molybdenum alloy or other suitable material. All surfaces which do not contact the femur 14 are preferably highly polished to provide smooth articulating bearing surfaces.

The tibial component 18 is adapted to be secured to the proximal end of the tibial 12 after the tibia has been resected in a manner known in the art. The tibial component 18 includes a substantially planar platform-like tibial tray 50 and an inferiorly extending tibial stem 52. The tibial stem 52 is adapted to be received in a corresponding opening made by the surgeon in the longitudinal center of the tibia 12. The tibial tray 50 and the tibial stem 52 define a conically shaped bore 54 axially extending through the tibial tray 50 and into the stem 52. The tibial tray or plateau 50 and stem 52 are preferably manufactured from cobalt-chromium-molybdenum or any other suitable biocompatible material. The top of the tibial tray 50 is highly polished to provide a substantially smooth tibial bearing surface 56.

The floating or rotating bearing 20 is located between the femoral component 16 and the tibial component 18. The floating bearing 20 has a substantially planar inferior bearing surface 58 which slidably moves relative to the highly polished tibial bearing surface 56, further discussed herein. The floating bearing 20 further includes a first superior articulating or bearing surface 59 and a second superior articulating or bearing surface 60. The first bearing surface 59 and the second bearing surface 60 articulate with the first bearing surface 26 of the condyle 22 and the second bearing surface 28 of the condyle 24 of the femoral component 16. Positioned between the first and second bearing surfaces 59 and 60 is a substantially rectangular opening 62 that is slidably positioned about a center modular guide post 64. The opening 62 is defined by a substantially perpendicular peripheral sidewall 66 which is operable to engage the center guide post 64. The floating bearing 20 is preferably formed from a surgical grade, low friction, low wearing plastic, such as UHMWPE or other suitable material.

The center guide post 64 includes a substantially oval shaped outer peripheral sidewall 68 or any other appropriately shaped sidewall and a conically tapered sidewall 70. The conically tapered sidewall 70 is operable to be nestingly received within the conically tapered bore 54 to provide a friction fit that forms a Morse-type taper. Alternatively, the center guide post 64 may be formed integral with the tibial component 18. Extending axially through the center guide post 64 is a substantially cylindrical bore 72 having a superiorly located counterbore 74, as shown clearly in FIG. 5a. The center guide post 64 is formed from a combination of a cobalt-chromium-molybdenum portion 76 and a molded polymer portion 78 formed from UHMWPE or other suitable material. The polymer portion 78 extends to the base of the tibial tray 50 to provide a polymer/polymer contact between the centering post 64 and the floating bearing 20, via sidewalls 66 and 68.

Axially extending through the bore 72 is a threaded bolt 80 which threadably engages a threaded bore 82 located inferiorly of the stem 52. The bolt 80 further includes a head 84 which is nestingly received within counterbore 74. The head 84 includes a hexagonal drive 86 that may be rotatably engaged by a hexagonal drive member. Upon threadably engaging bolt 80 within bore 82, the centering post 64 is rigidly secured, via the Morse-type taper formed from the conical bore 54 and the conical sidewall 70.

Referring to FIG. 5b, a second embodiment of a centering post 64' is shown. In this regard, like reference numerals will be used to identify like structures with respect to the centering post 64. The centering post 64' is substantially similar to the centering post 64 except that the metal portion 76' extends above the tibial tray 50, thereby providing a reduced or smaller polymer portion 78'. In this configuration, a polymer/metal contact or interface is formed between the floating bearing 20 and the centering post 64', via the sidewalls 66 and 68.

Turning to FIGS. 4 and 6, the articulating bearing surfaces 26 and 28 of the first and second condyles 22 and 24 of the femoral component 16 are shown cooperating with the bearing surfaces 59 and 60 of the floating bearing 20. In this regard, each condyle 22 and 24 of the femoral component 16 has a polycentric bearing surface 26 and 28, respectively along the sagittal plane. In other words, each bearing surface 26 and 28 is defined by a large anterior radius 80 and a smaller posterior/distal radius 82. The large anterior radius 80 is preferably about 1.497 inches and extends to about point 84. The posterior/distal radius 82 is about 0.945 inches and extends anterior the center line of the femoral component 16 up to point 84. Point 84 is located just anterior the floating bearing 20. Correspondingly, the bearing surface 59 and 60 of the floating bearing 20 are formed with a single radius 86 along the sagittal plane having a radius of about 0.945 inches. Because the sagittal posterior/distal radius 82 of the femoral component 16 extends beyond the axial center line of the femoral component 16 anteriorly to point 84, this radius congruently mates with the radius 86 of the floating bearing 20 from extension to full flexion. This mating provides a substantially fully mated and constant contact surface area between the femoral component 16 and the floating bearing 20 substantially through extension and flexion along the sagittal plane.

Each bearing surface 26 and 28 of the condyles 22 and 24 are arcuately shaped with a constant radius 88 of about 1.6 inches along the coronal plane. Correspondently, the bearing surfaces 59 and 60 of the floating bearing 20 are likewise, formed from a constant radius 90 of about 1.6 inches along the coronal plane. Each of the radii 88 and 90 congruently mate with one another to provide substantially full surface contact along the coronal plane from extension to flexion. This full surface contact along both the sagittal and coronal planes substantially evenly disburses stresses between the femoral component 16 and the floating bearing 20, as opposed to femoral components, which merely provide a smaller contact area, such as a line or point contact, either along the sagittal plane or the coronal plane which focuses stresses at these contact points, thereby potentially increasing wear in these areas. In other words, a contact area of greater than about 300 mm$^2$ is maintained from extension to full flexion between the femoral component 16 and the floating bearing 20.

Referring now to FIG. 7, a top view of the assembled tibial component 18, along with the floating bearing 20 is shown. In this regard, the floating bearing 20 has an outer peripheral wall 92 which is substantially concentric with the outer peripheral wall 94 of the tibial tray 50. With the floating bearing 20 positioned atop the tibial tray 50 in extension, the guide post 64 is positioned just posteriorly the opening 62 defined by sidewall 66. It should be noted that the post 64 is sized relative to the opening 62 such that the posterior stabilized knee joint prosthesis 10 provides anterior and posterior movement 96, medial to lateral movement 98, and rotation movement 100 of the floating bearing 20 relative to the tibial component 18. Moreover, the femoral component 16 provides rotational movement along the sagittal plane relative to the floating bearing 20, as well as varus and valgus movement relative to the floating bearing 20. The posterior stabilized knee joint prosthesis 10 may also simply provide the anterior to posterior movement 96 and the rotational movement 100 and eliminate the medial to lateral movement 98 of the floating bearing 20 relative to the tibial tray 50.

Turning to FIGS. 8a–8e, partial sagittal sectional views of the posterior stabilized (PS) knee joint prosthesis 10 illustrating the movement of the femoral component 16 and the floating bearing 20 relative to the tibial component 18 are shown from full extension in FIG. 8a to full flexion in FIG. 8e. In FIG. 8a, the posterior stabilized (PS) knee joint prosthesis 10, both anteriorly and posteriorly, is inherently stable at full extension when the patient is standing. In this position, the first and second femoral bearing surfaces 26 and 28 are rested within the first and second tibial bearing surfaces 59 and 60 of the floating bearing 20, respectively. The anterior surface 102 and the posterior surface 104 of the post 64 do not engage the anterior portion 106 or the posterior portion 108 of the sidewall 66. The posterior surface 104 of the post 64 further does not engage the engagement member 40 of the femoral component 16. If the knee joint prosthesis 10 would undergo a large hyperextension or forward rollback (approximately 10E), the anterior surface 102 of the post 64 would engage the anterior portion 38 of box 42 in the femoral component 16, while the floating bearing 20 would generally slide posteriorly relative to the tibial tray 50. This engagement will further avoid posterior dislocation of the femoral component 16 relative to the tibial component 18.

The femoral component 16 with respect to the tibial component 18 and the floating bearing 20 is generally most unrestricted between full extension, as illustrated in FIG. 8a and the point of flexion where the posterior engagement member 40 and the posterior surface 104 of the post 64 initially engage, as illustrated in FIG. 8b. This engagement generally occurs between about 20° to 45° of flexion. Within this range between 0° to about 20° to 45°, the femoral component 16 is permitted to translate in the sagittal plane along with the floating bearing 20 relative to the tibial component 18. In particular, the femoral component 16 will remain substantially congruently positioned relative to the floating bearing 20 to provide a full articulating contact surface during this range of flexion. In other words, the femoral component 16 and the floating bearing 20 are both able to move anteriorly and posteriorly relatively freely with respect to the tibial component 18, via the bearing surfaces 56 and 58 between the floating bearing 20 and the tibial tray 50. However, it should be further understood that the exact amount of translation in the sagittal plane permitted by the knee joint prosthesis 10 will of course, vary depending on the forces imparted by local soft tissues, muscles, tendons, ligaments, as well as forces transmitted from the tibia and fibula. These forces will, of course, vary from patient to patient, from activity to activity, as well as from implantation to implantation.

When flexion exceeds approximately 20° to 45°, as shown in FIG. 8c, the posterior engagement member 40 of the femoral component 16 engages the posterior surface 104 of the post 64. This engagement forces rollback of the floating bearing 20 posteriorly relative to the tibial tray 50, whereby the floating bearing 20 having bearing surface 58 slides relative to bearing surface 56 of tibial tray 50. While this forced rollback of the floating bearing 20 is occurring, the bearing surfaces 26 and 28 of the first and second condyles 24 and 26 are fully nestingly received within the bearing surfaces 59 and 60 of the floating bearing 20. This forced rollback of the floating bearing 20 creates the desired femoral rollback of an anatomical knee joint. As flexion continues from about 60° shown in FIG. 8c to about 110° shown in FIG. 8e, a forced rollback of the floating bearing 20 relative to the tibial tray 50 continues to occur, while a full surface contact area between the first and second condyles 22 and 24 and the floating bearing 20 are maintained, via cooperating surfaces 26, 28 and 59, 60, respectively.

As can be observed from FIGS. 8a–8e, the forced rollback provided by the engagement of the fixed modular post 64 with the engagement member 40 enables a full surface contact area to be maintained between the femoral component 16 and the floating bearing 20. This full surface contact is achieved because rollback is occurring between the floating bearing 20 and the tibial component 18, via a sliding of the floating bearing 20 posteriorly atop the tibial tray 50 with surfaces 56 and 58. This is in contrast to existing fixed bearing knee prostheses which achieve rollback, via the translation of the femoral component relative to a fixed bearing atop the tibial component. With conventional floating bearing knee prostheses, these devices either do not provide any type of guide post secured to the tibia and simply rely on soft tissue to produce the rollback or they utilize a post which is integral with the floating bearing. Accordingly, the rollback in the prior art is again occurring between the femoral component 16 and the floating bearing 20, as opposed to the floating bearing 20 and the tibial component 18, which provides a substantially increased surface area during rollback for overall reduced wear of the bearing member 20.

Turning to FIG. 9, a top view of the tibial component 18 and the floating bearing 20 is shown with a fully constrained guide post 110. In this regard, the post 110 is substantially similar to the post 64, except that the outer peripheral wall 112 is oval with truncated ends 114. In this regard, the endwalls 114 slidably engage the sidewalls 66 of opening 62, thereby eliminating any lateral or medial movement 98 or rotational movement 100 with respect to the tibial component 18. This fully constrained type knee therefore, only allows anterior and posterior movement 96 of the floating bearing 20 relative to the tibial component 18. Thus, by simply replacing the post 64 with a new post 110, the knee joint prosthesis 10 may be converted from a posterior stabilized (PS) knee joint prosthesis 10 to a fully constrained knee joint prosthesis 10'. This provides for a fully constrained knee that maintains the large contact area (i.e. >300 mm²), as well as having the desired rollback. It should further be noted that by simply changing the shape of the post 64, cam member 40, or the opening 62 in the bearing 20, the anterior motion may be adjusted. Moreover, removable sleeves may be fashioned that slide on to post 64 to provide for further adjustment.

This convertibility enables a substantially convenient method for changing from a posterior stabilized (PS) to a fully constrained knee joint by simply replacing the guide post 64, via the threaded bolt 80. Should further stability be required with the femoral component 16, a closed box femoral component 16' may be used which includes a femoral stem 116. In this situation, the original femoral component 16 would be replaced with the new femoral component 16', while the tibial component 18 and the bearing component 20 would stay the same. It should further be noted that the movement of the femoral component 16, the tibial component 18 and bearing member 20 relative to one another along the sagittal plane is substantially similar to that shown in FIGS. 8a–8e of the posterior stabilized (PS) knee joint prosthesis 10.

Turning to FIGS. 11 and 12, a primary knee joint prosthesis 120 according to the teachings of a third preferred embodiment of the present invention is shown. In this regard, the tibial component 18 and the floating bearing 20 are substantially the same as used with the other preferred embodiments. The only differences are with respect to the femoral component 122 and the central post 124. In this regard, the post 124 is substantially similar to the post 64 except that the height of the post is reduced so that it does not extend above or out beyond the opening 62. The femoral component 122 includes the first and second condyles 22 and 24 having the first and second bearing surfaces 26 and 28, respectively. The femoral component 122 further includes the articulating patella portion 48. What is essentially missing is the box 42 which provides the posterior engagement member 40. Because of this, there is no mechanical engagement of the post 124 relative to the femoral component 122 to force a rollback of the floating bearing 20 relative to the tibial component 18.

The rollback of the floating bearing 20 is achieved by the remaining soft tissues and ligaments of the patient. In this regard, the floating bearing 20 is initially centrally positioned about the tibial tray 50 similar to the other preferred embodiments during full extension. At about 25° to 45° of flexion, rollback of the floating bearing 20 starts and is substantially maintained through full flexion because of the cruciate ligament causing the floating bearing 20 to roll back. Here again, the primary knee joint prosthesis 120 may be converted from a primary knee joint prosthesis 120 to a posterior stabilized (PS) knee joint prosthesis 10 or a fully constrained knee joint prosthesis 10' by simply replacing the post 124 and the femoral component 122 without having to change the tibial component 18 or the tibial bearing 20.

Turning to FIG. 13, a partial sagittal sectional view of a posterior stabilized (PS) knee joint prosthesis 10" according to the teachings of a fourth preferred embodiment of the present invention is shown. In this regard, like reference numerals will be used to identify like structures with respect to the knee joint prosthesis 10. In this regard, the only differences are with respect to the shape of the guide post 130 and the floating bearing 132. The guide post 130 is secured to the tibial component 18 in substantially the same manner as that shown with regard to the knee joint prosthesis 10. The difference in the guide post 130 is that it includes a first guide portion 134 and a second guide portion 136. The first guide portion 134 is defined by a substantially oval shaped sidewall 138 similar to that shown in FIG. 2. The second guide portion 136 is also formed by an oval sidewall 140 which is larger than the oval sidewall 138. The first guide portion 134 is preferably formed from a molded polymer, such as UHMWPE and the second guide portion 136 is preferably formed from a cobalt-chromium-molybdenum. However, various other combinations between the first guide portion 134 and the second guide portion 136 can also be provided such as a complete polymer assembly, complete metallic assembly or any other combination.

The second guide portion 136 has a height which does not extend beyond the bearing 134 and is positioned within opening 142 such that the second guide portion 136 only engages and controls the movement of the floating bearing 132 relative to the tibial component 18. The second guide portion 134 extends into the box 42 of the femoral component 16 such that the second guide portion 134 is operable to be engaged by the cam member 40 to control the movement of the femoral component 16 relative to the bearing 132. In other words, the two stage guide post 138 individually controls the relative movement of the femoral component 16 and the bearing component 132 with the first guide portion 134 and the second guide portion 136, respectively. This provides for increased adjustability in the relative articulating motion of the knee joint prosthesis 10" while further maintaining a substantially full and continuous contact area between the femoral component 16 and the floating bearing 132 from extension to full flexion.

Referring to FIGS. 14–20, there is shown a posterior stabilized (PS) knee joint prosthesis 146 according to the teachings of a fifth preferred embodiment of the present invention which is designed to provide adequate stability in case of moderate deterioration or instability of the human knee. The knee joint prosthesis 146 is shown in FIG. 16 as being secured to a tibia 148 and a femur 150 of a surgically resected left knee joint, with the tibia 148 and the femur 150 shown in phantom, and with the understanding that a suitable right knee joint prosthesis can be similarly constructed. Here again, the knee joint prosthesis 146 includes a femoral component 152, a tibial component 154 and a floating tibial bearing 156.

The femoral component 152 is adapted to be secured to the distal end of the femur 150 similar to the femoral component 16, shown in FIG. 1. The femoral component 152 includes a first condylar portion 158 and a second condylar portion 160 that provides a first femoral bearing surface 162 and a second femoral bearing surface 164, respectively (see FIG. 17). Here again, the first and second condylar portions 158 and 160 are inter-connected by an inner condylar portion 166 that defines an inner condylar recess 168. The inner condylar portion 166 is defined by first and second lateral sidewalls 170 and 172, anterior wall 174, posterior engagement member or cam 176 and top 178. The top 178 may either be an open or closed top, depending upon the desired configuration.

The femoral component 152 also includes an arcuate patellar portion 180 which is disposed on the anterior surface of the femoral component 152. The patellar portion 180 is shaped to allow anatomical tracking of a natural or prosthetic patella. Again, the patella prosthesis, which are compatible with the present invention may be of varying shapes, such as round or dome shaped and may be constructed from polyethylene, polyethylene with metal backing or other suitable materials. Additionally, the femoral component 152 is preferably formed as a unitary structure and cast from a biocompatible high strength alloy, such as cobalt-chromium-molybdenum alloy or other suitable biocompatible material. The surfaces which do not contact the femur 150 are preferably highly polished to provide smooth articulating bearing surfaces.

The tibial component 154 is substantially similar to the tibial component 18 and is likewise adapted to be secured to the proximal end of the tibial 148 after the tibia 148 has been resected in a manner known in the art. The tibial component 154 includes a substantially planar plat form-like tibial tray 182 and an inferiorly extending tibial stem 184. The tibial stem 184 is adapted to be received in a corresponding opening made by a surgeon in the longitudinal center of the tibia 148. The tibial stem 184 is formed from a first planar member 186, which is positioned substantially perpendicular to the tibial plateau 182 and a second planar member 188 which is positioned at a slight angle relative to the perpendicular axis of member 186. Connecting member 186 with member 188 is a tapered member 190, which tapers at its distal end 192 to form a substantially I-beam cross-section.

The tibial tray 182 and the tibial stem 184 define a conically shaped bore 194. Here again, the tibial tray 182 and the tibial stem 184 are preferably manufactured from cobalt-chromium-molybdenum, or any other suitable material with the top of the tibial tray 182 being highly polished to provide a substantially smooth tibial bearing surface 196.

The floating bearing 156 is positioned between the femoral component 152 and the tibial component 154. The floating bearing 156 includes a substantially planar inferior bearing surface 198 which slidably moves relative to the highly polished tibial bearing surface 196. The floating bearing 156 also includes a first superior articulating or bearing surface 200 and a second superior articulating or bearing surface 202. Positioned between the first and second bearing surfaces 200 and 202 is an elongated opening 204 that is slidably positioned about a guide post 206. The opening 204 is defined by a pair of opposed lateral sidewalls 208, a semi-circular or arcuate posterior sidewall 210 and an anterior sidewall 212 which has a pair of recessed lobes or ears 214. Extending posteriorly from the opening 204 is a recessed area 216 positioned or located between the first bearing surface 200 and the second bearing surface 202. The floating bearing 156 is also preferably formed from a surgical grade, low friction, low wearing plastic, such as UHMWPE or other suitable material.

The center guide post 206 includes a substantially cylindrically shaped outer peripheral sidewall 218 and a conically tapered sidewall 220. The conically tapered sidewall 220 is operable to be nestingly received within the conically tapered bore 194 to provide a friction fit formed by a Morse-type taper. It should further be noted that guide post 206 may also be formed integral with the tibial component 154. The guide post 206 is constructed from a combination of a cobalt-chromium-molybdenum portion 222 and a molded polymer portion 224 formed from UHMWPE or other suitable material. The non-polymer portion 222 extends up to the floating bearing 156 so that the floating bearing 156 contacts the cobalt-chromium-molybdenum cylindrical sidewall 218. The polymer portion 224 is molded to a post 226 and extends from above the floating bearing 156 into the recess 168, also having the outer cylindrical sidewall 218. The superior surface of the guide post 206 has an anterior arcuate surface 228 and planar tapered superior sidewalls 230. The anterior arcuate sidewall 228 reduces or eliminates impingement of the post 206 within the inner condylar portion 166 during hyper-extension of the knee joint prosthesis 146. The cylindrical sidewall 218 also includes a posterior planar sidewall portion 231, further discussed herein.

Extending through the center guide post 206 is a substantially cylindrical axial bore 232 having a stepped shoulder 234. The stepped shoulder 234 forms a retention mechanism to retain a threaded bolt 236 within the axial bore 232. In this regard, the non-polymer portion 222 of the guide post 206 is machined and tooled in the configuration shown. The threaded bolt 236 which includes a head 238 having a hexagonal drive 240 is then inserted into the bore 232. Thereafter, the polymer portion 224 is molded over the elongated post 226 with the subsequent bore 232 being formed therein to create the shoulder 234. The shoulder 234 captures or retains the bolt 236 within the non-polymer portion 222 of the center guide post 206. In this way, should the bolt 236 ever become loosened from threaded bore 242, it will not be free to enter the articulating area of the knee joint prosthesis 146. Thus, to rigidly secure the center guide post 206, the tapered sidewall 220 is matingly received within the tapered bore 194 and the bolt 236 is threadably engaged within bore 242 to securely hold the centering guide post 206 relative to the tibial component 154.

Figure 21:
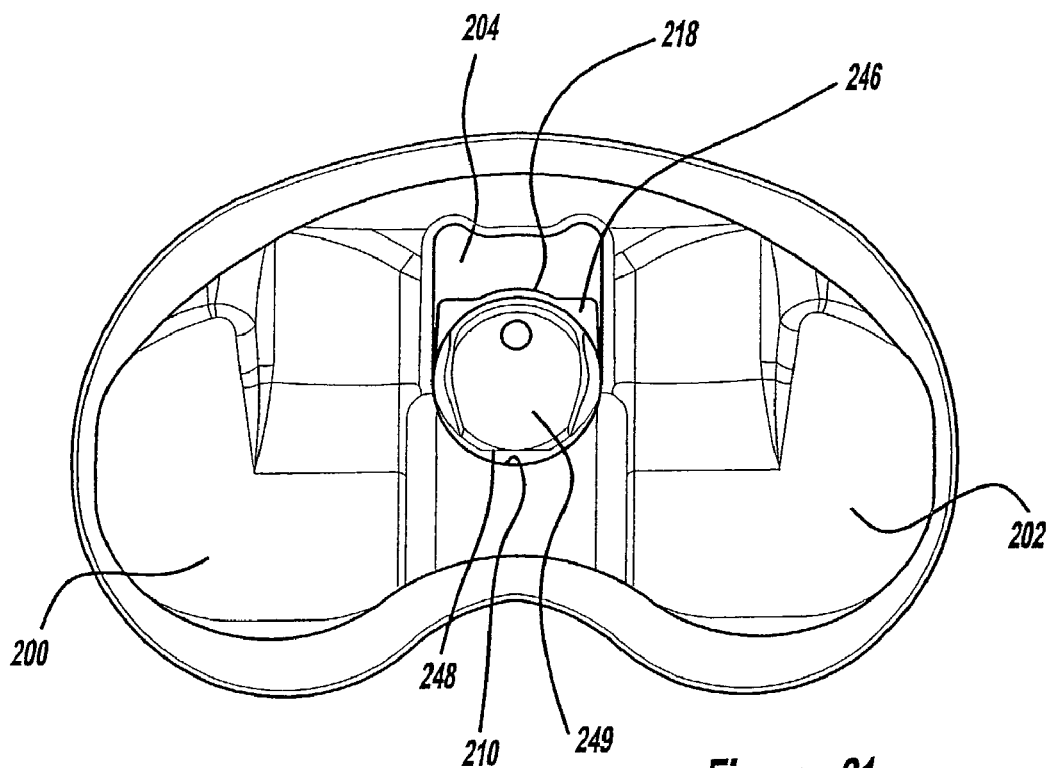
FIG. 21 is a top view of an assembled tibial component and bearing member according to the teachings of a sixth preferred embodiment of the present invention.

Referring to FIG. 21, another embodiment of a centering post 244 is shown. In this regard, like reference numerals will be used to identify like structures with respect to the centering post 206. The centering post 244 is substantially similar to the centering post 206, except that the non-polymer portion 222 of the cylindrical sidewall 218 includes a pair of arcuate lobes or ears 246 which extend anteriorly from the post 244. The arcuate lobes 246 extend anteriorly in the region of the floating bearing 146 and do not extend up beyond this region into the recess 168 of the femoral component 152, thereby providing two guide portions or regions in the guide post 244. It should also be noted that the arcuate lobes 246 may also extend posteriorly and achieve substantially the same level of rotational constraint as the anterior extending lobes 246. The guide post 244 also includes a posterior planar sidewall 248 extending throughout the length of the sidewall 218. This planar sidewall region 248 inhibits contact of the post 244 relative to the posterior sidewall 210 of the opening 204 formed within the bearing 156. In this regard, by preventing contact at the posterior most portion of the opening 204 where the thickness of the bearing wall is the thinnest, this disburses the force imparted by the post 244 to the thickest regions of the bearing 156, thereby enhancing distribution of the engagement force between the post 244 and the bearing 156.

The guide post 244 enables the bearing 156 to move anterior-posterior (A-P), as well as enables rotational movement of the bearing 156 relative to the tibial component 154, similar to the guide post 206. However, by providing the additional arcuate lobes 246, rotational movement is substantially limited to about +/−15°. In this regard, upon rotating the bearing 156 relative to the fixed post 244, the lateral sidewall 208 of the opening 204 will engage one of the arcuate lobes 246 upon rotation of about 15°, thereby preventing further rotation of the bearing member 156 relative to the guide post 244. This provides a more constrained knee joint prosthesis 146 as compared to the guide post 206. Therefore, by simply switching the guide post 206 with the guide post 244, the rotational translation of the knee joint prosthesis 146 can be changed or constrained to about +/−15°, while still providing the same A-P translation.

Figure 22:
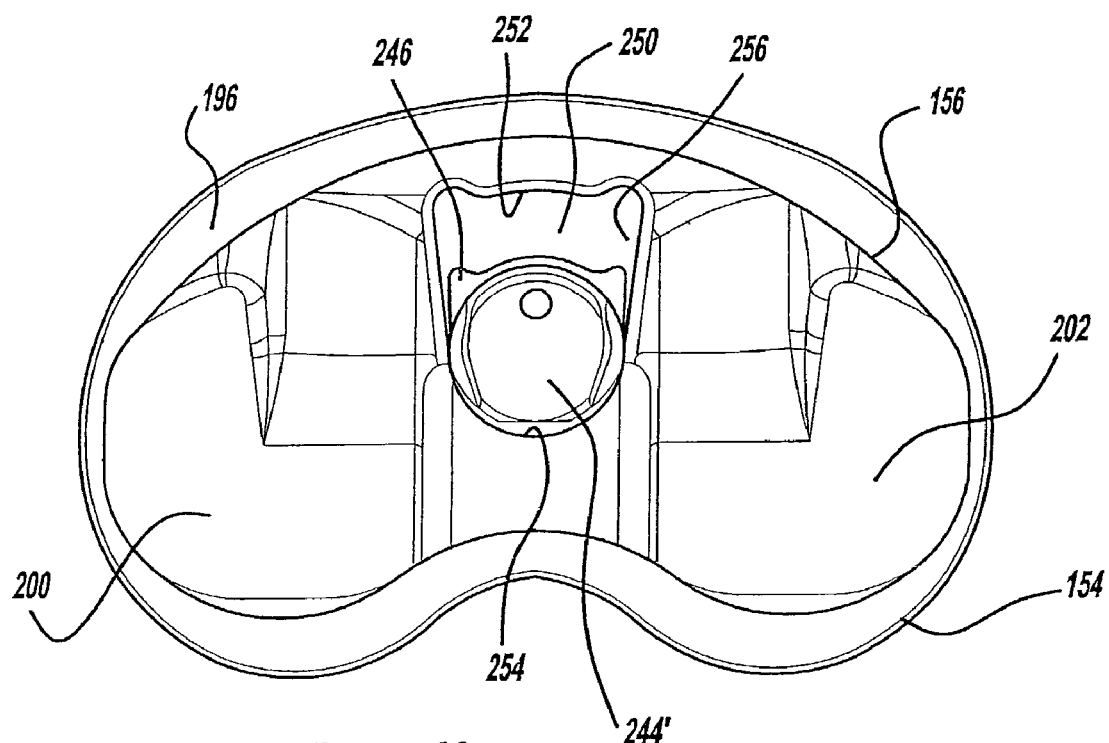
FIG. 22 is a top view of an assembled tibial component and bearing member according to the teachings of a seventh preferred embodiment of the present invention.

Referring now to FIG. 22, a guide post 244' is shown in use with the bearing 156 having a different shaped opening 250. In this regard, the opening 250 includes an anterior sidewall 252, a posterior sidewall 254 and a pair of angled lateral sidewalls 256. The angled lateral sidewalls 256 narrow the opening 250 posteriorly and widen the opening 250 anteriorly. With this configuration, when the knee joint prosthesis 146 is in extension, the guide post 244' somewhat engages the posterior sidewall 254 with the arcuate lobes 246 substantially aligning with the angled lateral sidewalls 256, such that there is little or no rotation of the bearing 156 relative to the post 244' in extension. As there is flexion of the femoral component 152 relative to the tibial component 154, the bearing 156 is forced posteriorly, further discussed herein, such that the guide post 244' enters the widened recessed area between the lateral sidewalls 256. As the bearing 156 is forced further posteriorly, further rotational freedom of movement is provided for the bearing 156 relative to the guide post 244', as well as medial to lateral movement during this A-P translation, thereby providing a less constrained knee joint prosthesis 146 with increased flexion. This type of constraint closely mimics an anatomical knee joint. Therefore, by simply changing the style bearing component or opening formed within the bearing 156, varying constraint may be achieved.

Referring back to FIGS. 17 and 18, the articulating bearing surfaces 162 and 164 of the first and second condyles 158 and 160 of the femoral component 152 are shown cooperating with the bearing surfaces 200 and 202 of the floating bearing 156. Each condyle 158 and 160 of the femoral component 152 has a polycentric bearing surface 162 and 164, respectively along the sagittal plane. In this regard, each bearing surface 162 and 164 is defined by a large anterior radius 260 and a smaller posterior/distal radius 262. Point 264 is located just anterior the contact area of the floating bearing 156. Because of this, the bearing surfaces 200 and 202 of the floating bearing 156 are formed with a single radius along the sagittal plane that corresponds to the posterior/distal radius 262. The posterior radius 262 of the condyles 158 and 160 extends up to point 264 cutting into a region of the condyles 158 and 160 to form a pair of opened anterior cavities or regions 268. These opened cavities 268 are positioned above the contact areas of the floating bearing 156 in extension and engage stop regions 270 of the floating bearing 156 during hyper-extension. Correspondingly, the bearing 156 further includes inner regions 272 which engage the inner regions 274 of the condyles 158 and 160 only during hyper-extension. Thus, in extension, the opened anterior cavities 268 are positioned above the stops 270 to eliminate conformity in this region, thereby substantially reducing soft tissue impingement in this area. Contact between the stop region 270 and the anterior cavities 268 only occur during hyper-extension of the knee joint prosthesis 146.

Figure 20A:
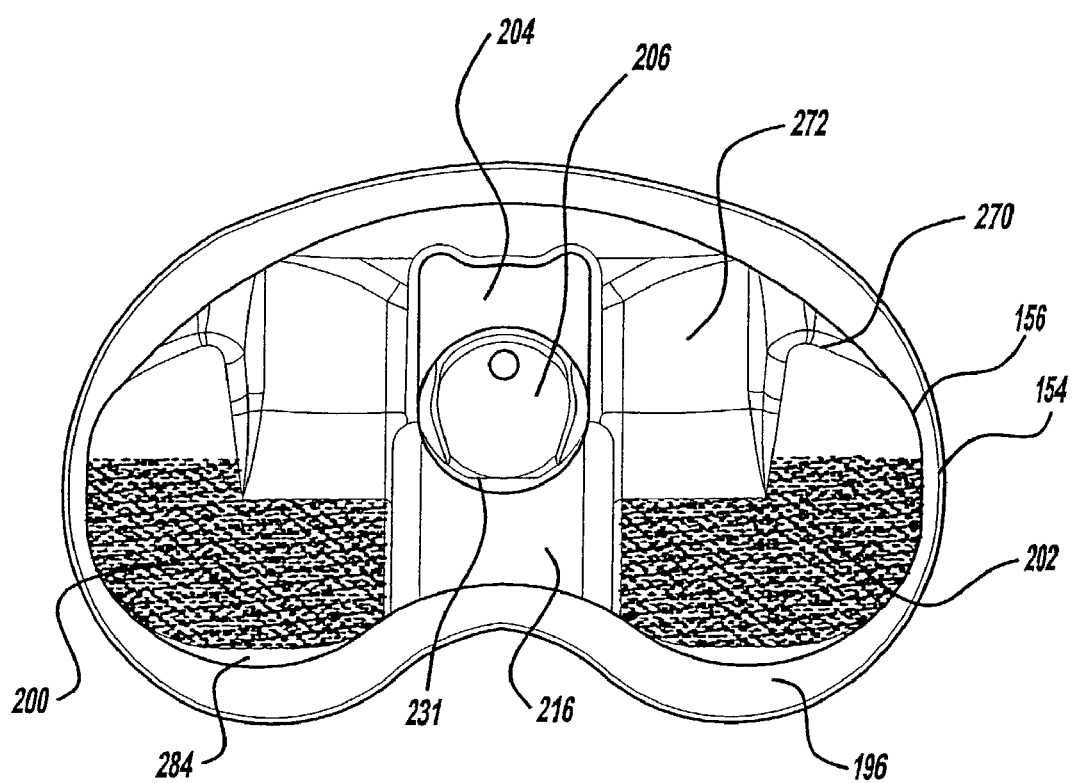
FIGS. 20a–20b are top views of the assembled tibial component and bearing member of FIG. 14 identifying shaded the contact areas in extension and flexion.
Figure 20B:
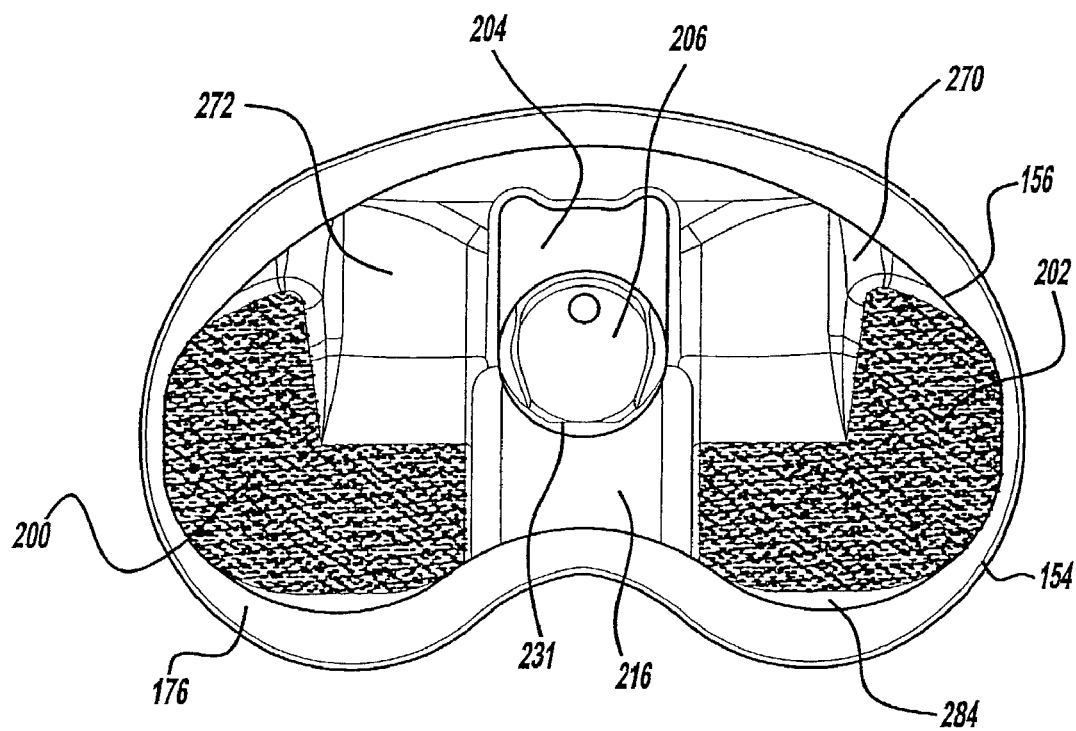

Each bearing surface 162 and 164 of the condyles 158 and 160 are also arcuately shaped with a constant radius 276, along the coronal plane. Correspondingly, the bearing surfaces 200 and 202 of the floating bearing 156 are likewise, formed from a similar constant radius 278 along the coronal plane of the floating bearing 156. Each of the radii 276 and 278 congruently mate with one another to provide a large surface contact area along the coronal plane which increases as flexion increases. In this regard, referring to FIGS. 20a and 20b, the contact area on the floating bearing 156 with the condyle bearing surfaces 162 and 164 in extension are shown shaded in FIG. 20a. It can clearly be observed that a portion of the bearing surfaces 200 and 202 of the floating bearing 156 are in contact with the condyles 158 and 160, except for the stop areas 270 and the inner areas 272, which are only engaged in hyper-extension. In FIG. 20b, the contact area along the floating bearing is shown shaded during flexion of 18° to 110° which illustrates that the contact area increases during flexion to provide further support and less wear of the bearing 156. This surface contact along both the sagittal and coronal planes substantially evenly disburses stresses between the femoral component 152 and the floating bearing 156.

Referring again to FIG. 19, a top view of the assembled tibia component 154, along with the floating bearing 156 is shown. In this regard, the floating bearing 156 has an outer peripheral wall 280 which is substantially concentric with the outer peripheral wall 282 of the tibial tray 182. The outer peripheral wall 280 of the floating bearing 156 also includes a pair of posterior lip extensions 284 which extend out along the bearing surface 198 of the floating bearing 156 (see FIG. 18). This pair of lip extensions 284 eliminates undesirable moment arms as the femoral component 152 moves posterior and rolls up the posterior portion of the center guide post 206 during extreme flexion (see FIG. 23d). In other words, by having the superior articulation or bearing surfaces 200 and 202 extend less posteriorly than the inferior articulation or bearing surface 198, the undesirable moment arm about the floating bearing 156 is eliminated. It should also be noted that a chamfer on the superior surface of the floating bearing 156 may also achieve this or any other configuration as long as the inferior articulation extends posteriorly more than the superior articulation. Therefore, the floating bearing 156 is substantially inhibited from tilting superiorly based upon the moment arms generated upon such flexion. With the floating bearing 156 positioned atop the tibial tray 182 in extension, the guide post 206 is positioned substantially posteriorly of the opening 204, such that the posterior stabilized knee joint prosthesis 146 provides anterior and posterior movement and rotational movement of the floating bearing 156 relative to the tibial component 154. Also the femoral component 152 provides rotational movement along the sagittal plane relative to the floating bearing 156, as well as varus and valgus movement relative to the floating bearing surface 156. It should further be noted that by simply changing the post configuration or the opening configuration, various types of constraints may be easily accommodated.

Figure 23A:
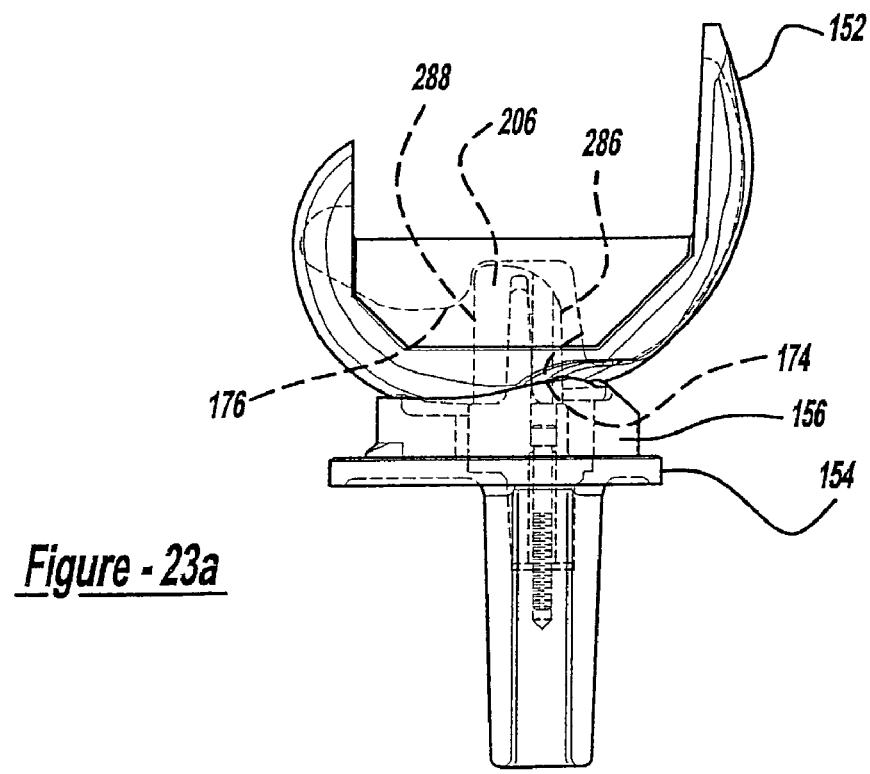
FIGS. 23a–23d are partial sagittal section views of the posterior stabilized (PS) knee joint prosthesis shown in FIG. 14 illustrating four different positions of the femoral component with respect to the tibial component during a range of fluxion from full extension to 110° of fluxion.
Figure 23B:
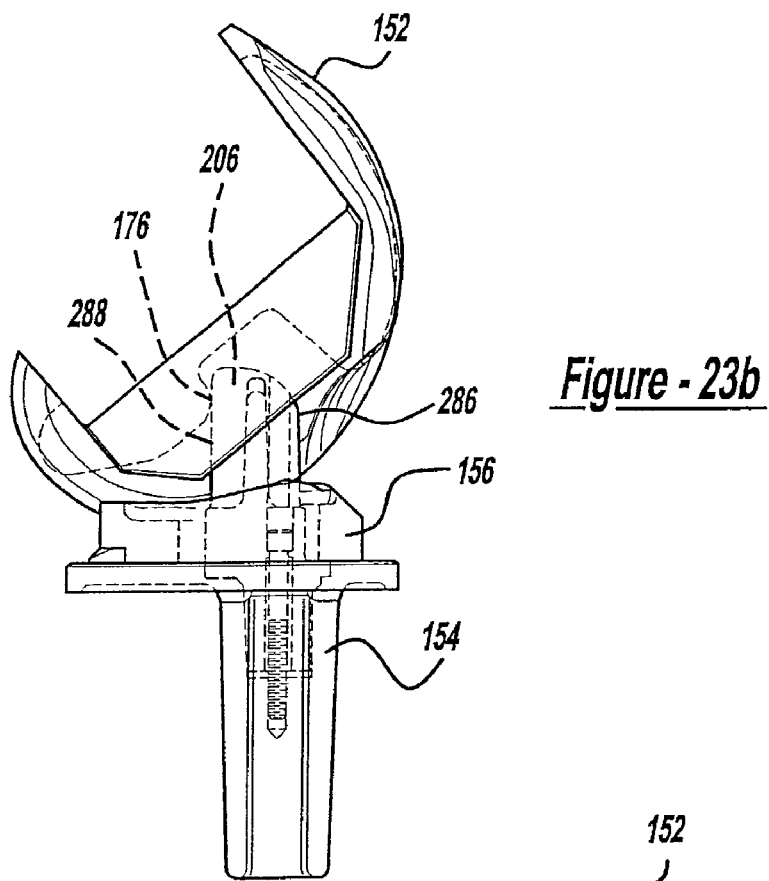
Figure 23C:
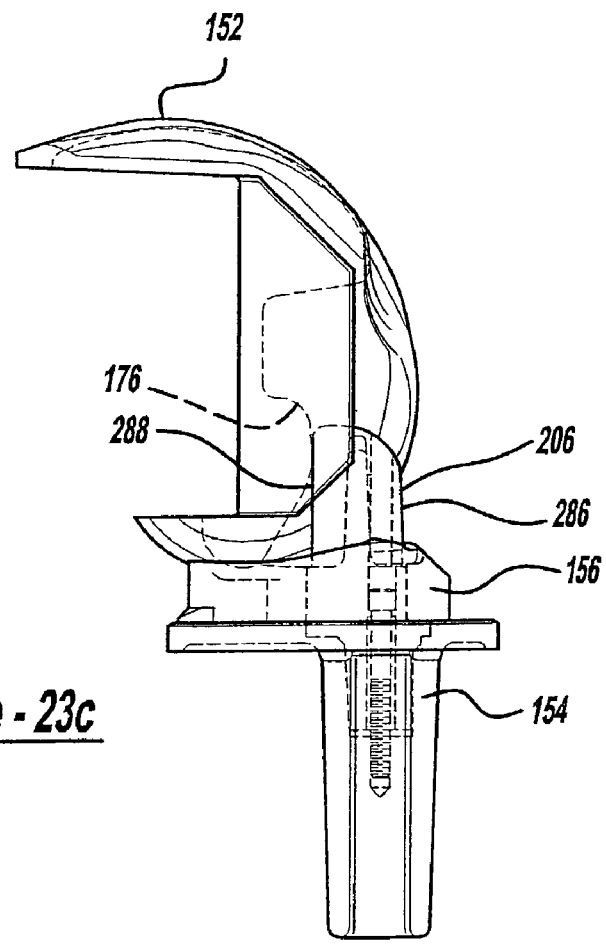
Figure 23D:
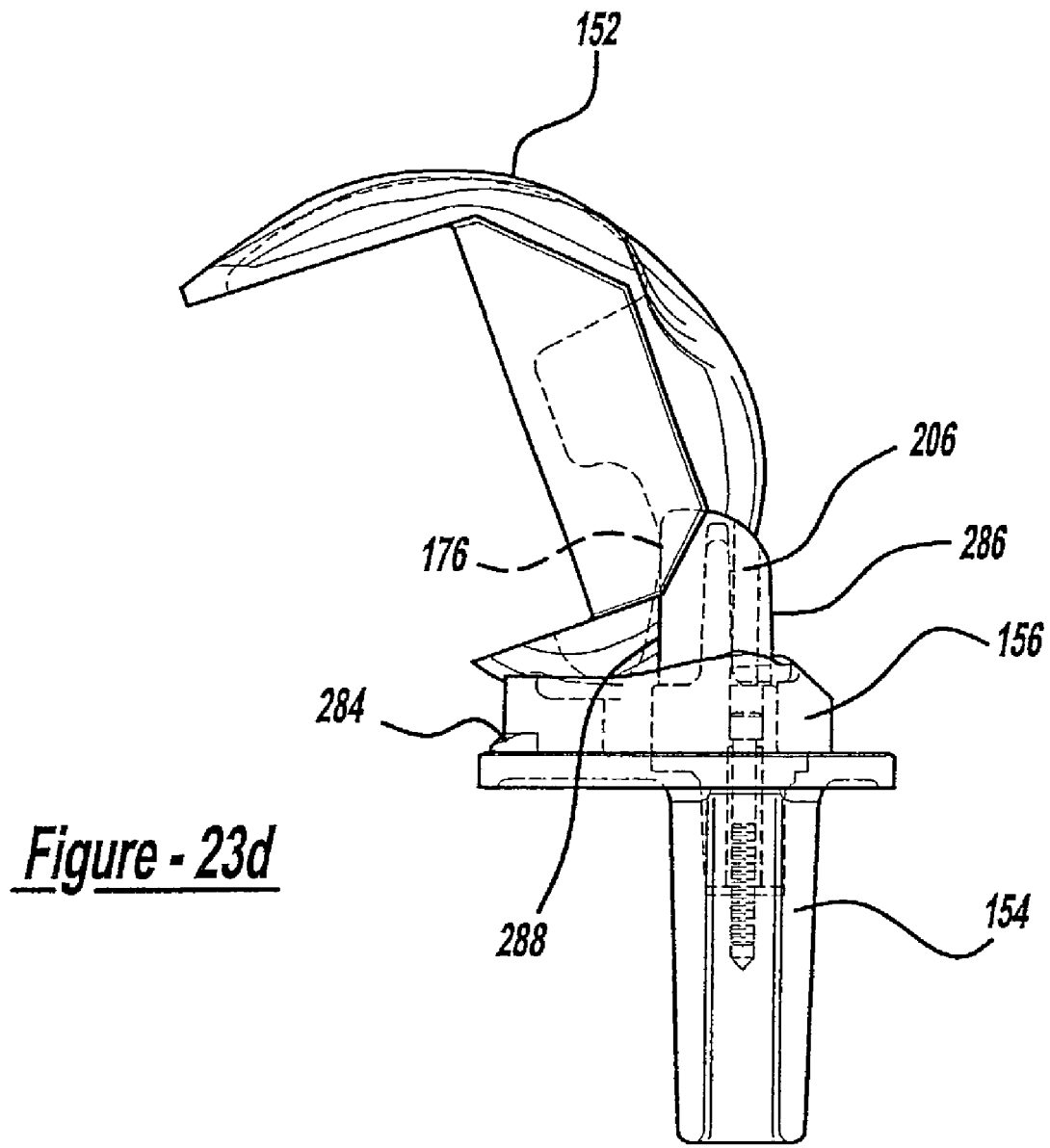

Finally referring to FIGS. 23a–23d, partial sagittal sectional views of the posterior stabilized (PS) knee joint prosthesis 146 illustrating the movement of the femoral component 152 and the floating bearing 156 relative to the tibial component 154 are shown from extension in FIG. 23a to flexion of 110° in FIG. 23d. In FIG. 23a, the posterior stabilized (PS) knee joint prosthesis 146, both anteriorly and posteriorly, is inherently stable at full extension when the patient is standing. In this position, the first and second femoral bearing surfaces 162 and 164 are nested within the first and second tibial bearing surfaces 200 and 202 of the floating bearing 156, respectively. Additionally, the stop portions 270 are not in contact with the anterior cavities 268 in the femoral component 152 to inhibit soft tissue impingement in this region during extension. At 0° flexion, the anterior surface 286 and the posterior surface 288 of the guide post 206 is generally not in engagement with the anterior sidewall 212 or the posterior sidewall 210 of the opening 204 or with the posterior cam 176 or the anterior wall 174 of the inner condylar portion 166. Should the knee joint prosthesis 146 undergo a large hyper-extension (approximately 10°), the anterior surface 286 of the guide post 206 would engage the anterior sidewall 174 of the inner condylar portion 166. The pair of anterior cavities 268 of the femoral component 152 would also engage the stops 270 of the bearing 156, while the inner condylar bearing surfaces 274 would engage the inner surfaces 272 of the floating bearing 156. This engagement will avoid posterior dislocation of the femoral component 152 relative to the tibial component 154.

As flexion of the knee joint prosthesis 146 occurs, the posterior cam 176 will generally engage the posterior side 288 of the post 206 at about 40° of flexion, as shown in FIG. 23b. Before this engagement, the femoral component 152, the tibial component 154 and the floating bearing 156 is generally most unrestricted, such that the femoral component 152 is permitted to translate in the sagittal plane along with the floating bearing 156 relative to the tibial component 154. Upon engagement of the cam 176 relative to the posterior side 288 of the post 206, the floating bearing 156 rolls back posteriorly relative to the tibial tray 182. This causes the floating bearing 156, having bearing surface 198, to slide relative to the bearing surface 196 of the tibial tray 182. While this forced rollback of the floating bearing 156 is occurring, the bearing surfaces 162 and 164 of the femoral component 152 are nestingly received within the bearing surfaces 200 and 202 of the floating bearing 156 (shown highlighted in FIG. 20b).

As flexion continues to about 90°, shown in FIG. 23c, a forced rollback of the floating bearing 156 relative to the tibial tray 182 continues to occur while the contact area between the femoral component and floating bearing increases as shown in FIG. 20b. Upon flexion reaching about 110°, the femoral component 156 moves posteriorly and rolls up upon the posterior side 288 of the guide post 206 reducing the contact area between the femoral component 152 and the bearing 156. The posterior lip extension 284 prevent the floating bearing 156 from flipping up or tipping superiorly during this phase of flexion by reducing the moment arm about the contact point of the posterior cam 176 to the contact surface between the femoral component 152 and the floating bearing 156.

As can be observed from FIGS. 23a–23d, forced rollback provided by the engagement of the fixed modular guide post 206 with the cam 176 provides a surface contact area between the femoral component 152 and the floating bearing 156 which increases as flexion increases (see FIGS. 20a–20b), until extreme flexion (i.e., ≧110°). Moreover, by providing engagement of the cam 176 with the guide post 206 at about 40° of flexion, wear on the guide post 206 is substantially reduced because the post/cam contact occurs after the loading phase of normal gait. In addition, by delaying the cam engagement until after the loading phase of gait, the cam 176 contacts the guide post 206 closer to the tibial/femoral articulation or lower along the guide post 206. This lower contact point reduces the moment arm on the guide post 206, and therefore, the stresses on the guide post 206. It should further be noted that the guide post 206 maintains the position of the bearing 156 from 0° to 40° of flexion since tibial or femoral congruency is maintained and the bearing cannot slide forward with the posterior surface of the opening, engaging the posterior side 288 of the post 206. Finally, since the highest load placed on the quad mechanism or muscle occurs during stair climbing or after 40° of flexion and the cam 176 engages the post 206 at 40°, this forces the rollback to maintain at least physiological rollback and extension moment arm values, thereby enabling patients to perform high demand activities without altering their gait or posture to compensate for a compromised quad mechanism.

Figure 24:
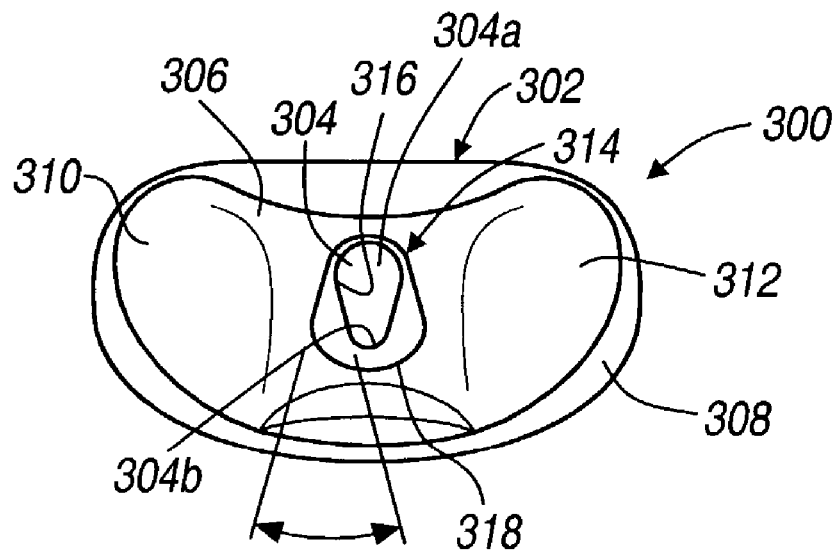
FIG. 24 is an elevational view of a tibial component including a bearing component according to an alternative embodiment of the present invention.
Figure 25:
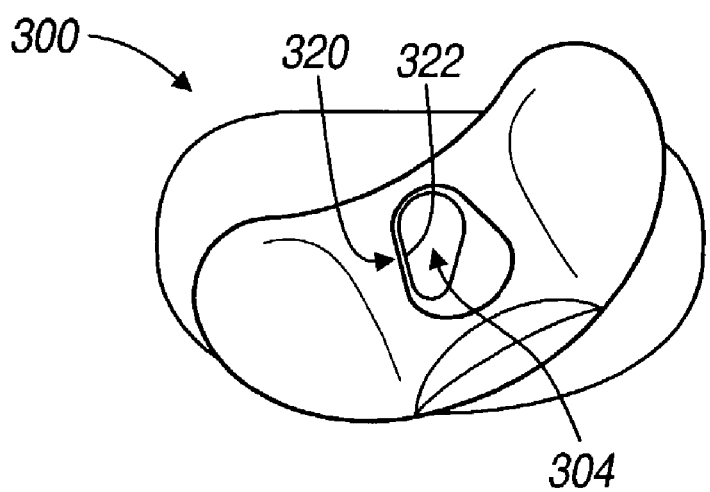
FIG. 25 is an elevational view of the component of FIG. 24 where the bearing component is rotated.
Figure 26:
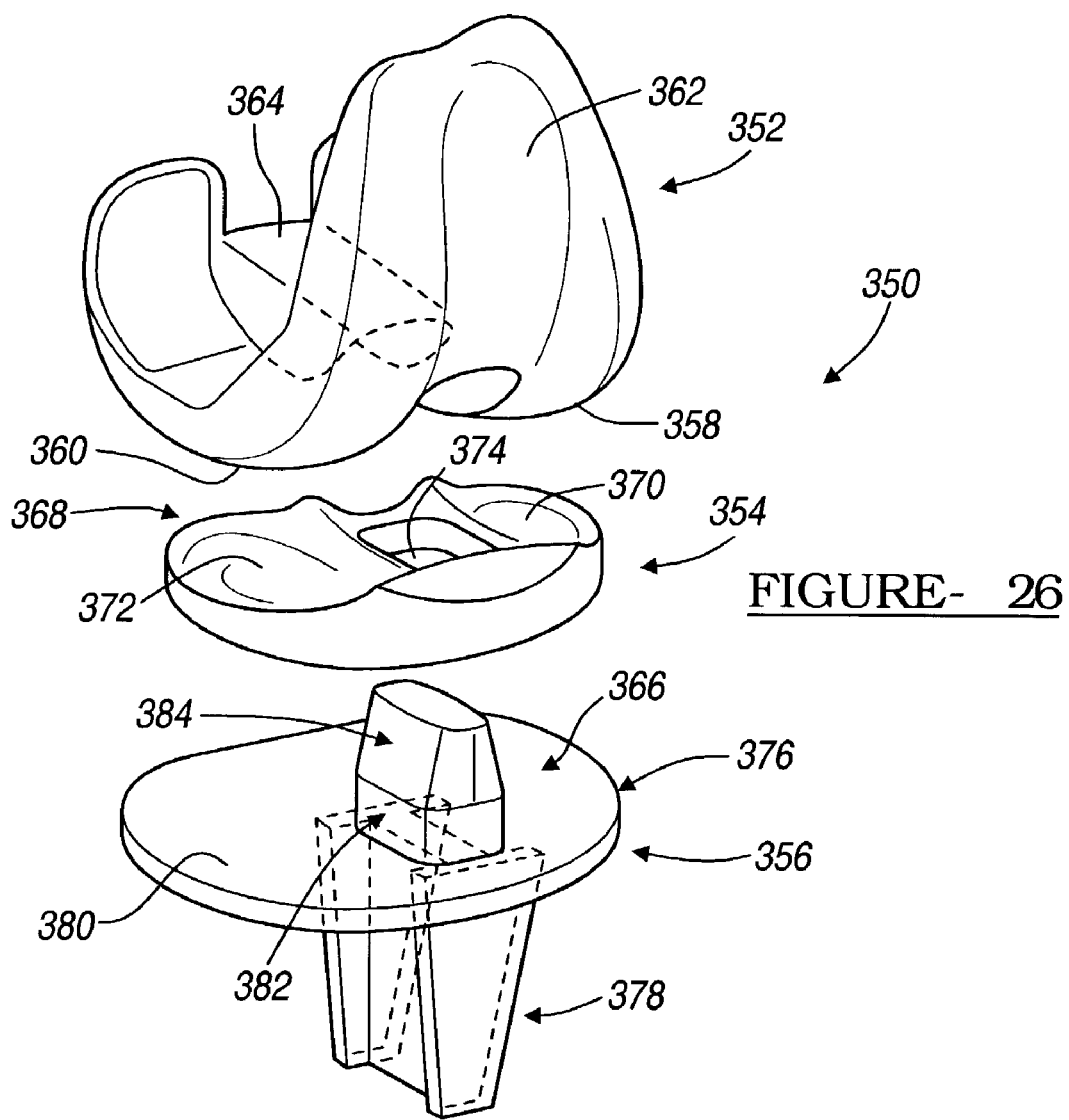
FIG. 26 is an exploded perspective view of a knee prosthetic according to an alternative embodiment of the present invention.

Referring to FIGS. 24 and 25, there is shown an additional embodiment of a tibial component 300, which may be used in place of the tibia component described above in conjunction with a posterior stabilized (PS) knee joint prosthesis, which is used to provide adequate stability in case of moderate deterioration instability of the human knee, as described above. It will be understood that although a femoral component is not illustrated, in conjunction with the tibial component 300, an appropriate femoral component as disclosed above may be implanted in the femur to articulate with the tibial component 300 to provide the desired PS knee prosthesis. The tibial component 300 includes a tibial tray 302. A posterior stabilizing post (PS post) or guide post 304 extends superiorly from the tibial tray 302. The guidepost 304 may be either formed integrally with the tibial tray 302, or may be modular and affixed to the tibial component 300 similar to that illustrated in FIG. 15 above. The PS post 304 includes a generally tear drop or pear shape cross-section, such that a posterior portion 304a of the PS post 304 has a longer or larger arc length than an anterior portion 304b of the PS post 304.

A bearing component 306 is disposed superiorly of the tibial tray 302. The superior side of the tibial tray 302 defines a tibial tray bearing surface 308. An inferior side of the bearing component 306 may articulate with the tibial tray bearing surface 308. A superior side of the bearing component 306 defines femoral bearings including a first condylar bearing surface 310 and a second condylar bearing surface 312. It is understood the tibial component 300 may be placed in either the right or left knee of a patient. The bearing component 306 also defines a bearing hole or bore 314. The bearing hole 314 includes at least a posterior wall or section 316 and an anterior wall or section 318. Generally, the posterior wall 316 includes a smaller arc length than that of the anterior wall 318.

The bearing hole 314 has an area or perimeter greater than the perimeter of the PS post 304. Therefore, the bearing member 306 is free to slide or articulate on the tibial tray bearing surface 308 when implanted in a knee. Nevertheless, the motion of the bearing component 306 is restricted by the presence of the PS post 304. In particular, the bearing component 306 is able to move anterior and posterior, medial/lateral, and rotate around the PS post 304. The inclusion of the bearing hole 314 allows for at least three degrees of freedom of the bearing component 306 while the PS post 304 limits the range of motion within each degree.

Illustrated particularly in FIG. 25, the bearing component 306 is moved to its most anterior position and rotated to its maximum laterally rotated position. At this point, a medial wall 320 of the bearing hole 314 engages a medial side 322 of the PS post 304. While a posterior wall 324 of the bearing hole 314 engages a posterior side 326 of the PS post 304. The shapes of the PS post 304 and the bearing hole 314 determine the amount of articulation allowed of the bearing component 306. Therefore, increasing the anterior to posterior length of the PS post 304 reduces the amount of anterior and posterior movement of the bearing 306 component. Decreasing anterior to posterior length of the post 304 increases the amount of anterior and posterior articulation of the bearing component 306. Nevertheless, the inclusion of both the tear drop shaped bearing hole 314 and the PS post 304 having the inverse tear drop shape provides a controlled and constrained movement of the bearing component 306, while still allowing for the various degrees of freedom. The complementary shapes of the bearing hole 314 and the PS post 304 limit the amount of rotation of the bearing component 306. Again, the relative size of the bearing hole 314 and the PS post determine the limitation of rotation. In other words, as the bearing component 306 moves posterior, rotational movement of the bearing component 306 relative to the tibial tray 302 is limited.

Referring to FIGS. 26–28a, a seventh embodiment of a posterior stabilized knee (PS) 350 is illustrated. The PS knee 350 includes the general advantages of the preceding embodiments wherein the PS knee prosthesis 350 allows for a general stabilization of a weakened natural knee. The PS knee prosthesis 350 generally includes a femoral component 352, a bearing component 354 and a tibial component 356.

The femoral component 352 includes a first condylar portion 358 and a second condylar portion 360. It is understood that the PS knee prosthesis 350 may also be implanted into either a left knee or a right. The femoral component 352 also includes a patellar groove 362, which allows for a generally natural articulation of a patella or patellar implant. In addition, between the first condylar portion 358 and the second condylar portion 360, a box 364 is provided. The box 364 substantially closes the central portion of the femoral component 352 and provides a cam surface for a posterior stabilizing (PS) post 366 described more fully herein.

The bearing component 354 includes a femoral bearing superior side 368, which includes a first superior articulating or bearing surface 370 and a second superior articulating or bearing surface 372. Defined by the bearing component 354, and positioned between the first bearing surface 370 and the second bearing surface 372, is an elongated opening 374 adapted such that the PS post 366 may extend through the bearing opening 374.

The tibial component 356 includes a substantially planar platform or tibial tray 376 and an inferiorly extending tibial stem 378. The tibial stem 378 is formed substantially similar to the tibial stem 184 described in relation to the fourth embodiment of the present invention. The anterior surface of the tibial tray 376 is a tibial tray bearing surface 380. The tibial component 356 may generally be made of titanium, cobalt chromium alloys, or other suitable biologically compatible metallic alloys. The tibial tray bearing surface 380 is generally highly polished to allow for a smooth articulation between the tibial tray bearing surface 380 and the bearing component 354.

Extending superiorly from the tibial articulating surface 380 is the PS post 366. Although the PS post 366, illustrated here, is formed integrally with the tibial tray 376, it will be understood that the PS post 366 may be modular and affixed to the tibial component 356 with an appropriate means, such as that disclosed above. The PS post 366 generally includes an inferior portion 382, and a superior portion 384. The inferior portion 382 has a cross-section, that allows the bearing component 354 to articulate, and rotate on the tibial tray bearing surface 380. The superior portion 384 is pyramidal or oval-conical in shape. That is, generally the superior portion 384 includes an anterior posterior (or sagittal plane) length that is greater than a medial to lateral (or coronal plane) width of the superior portion 384. Although this shape is exemplary, other shapes such as ovals tapering to the inferior portion 382 may also be used. The superior portion 384 is tapered along the sagittal plane towards a superior end, such that the superior end is smaller than the inferior end. The taper allows the femoral component to distract varus and valgus, as discussed further herein, when it is in a substantially non-rotated or non-engaged position. Nevertheless, when it is rotated the superior portion 384 of the PS post 366 limits the varus or valgus distraction of the femoral component 352. This is done by contacting or engaging a portion of the side walls of the intercondylar box 364 to reduce the freedom of the femoral component 352 relative the tibial component 356.

The anterior to posterior dimension of the superior portion 384 is equal to or greater than the medial to lateral width of the box 364. The medial to lateral width of the superior portion 384 is less than the medial to lateral width of the box 364. In this way, the femoral component 352 may rotate relative the tibial component 356. Moreover, when the femoral component 352 is substantially contacting the bearing component 354 and the bearing component 354 is substantially contacting the tibial tray bearing surface 380, this defines a substantially undistracted position of the knee, where the femoral component 352 may rotate with substantial freedom. Moreover, when the femoral component is 352 is not rotated it may also have relatively large amounts of varus and valgus distraction.

Figure 27:
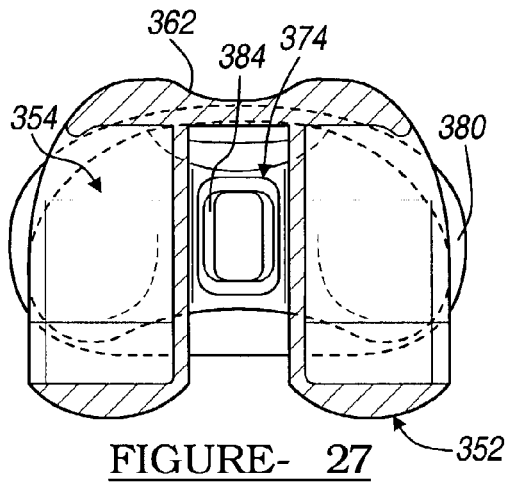
FIG. 27 is a partial section elevational view of the knee prosthetic of FIG. 26 in a neutral or zero degree rotation position.
Figure 27A:
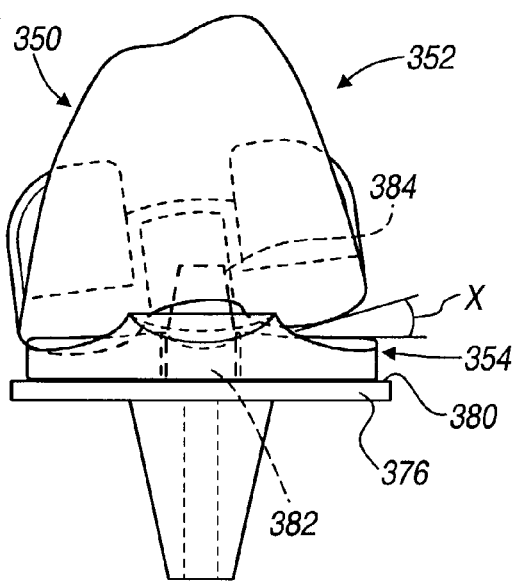
FIG. 27a is an front elevational view of the knee prosthetic of FIG. 26 with a predetermined amount of varus distraction.
Figure 28A:
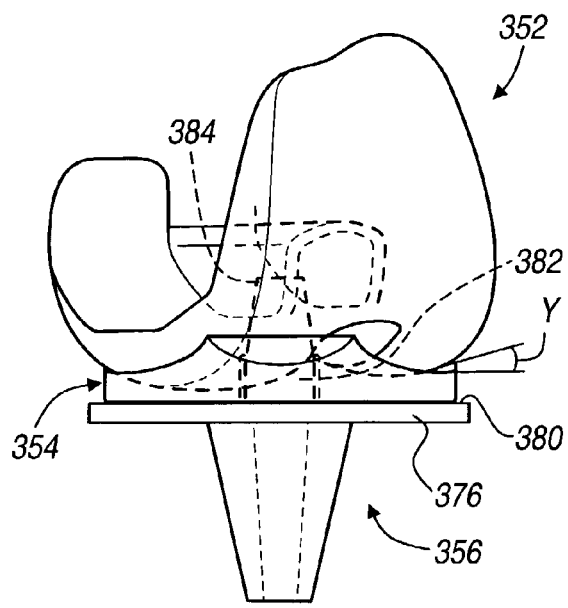
FIG. 28a is a front elevational view of the knee prosthetic illustrated in FIG. 28 showing a limited amount of varus distraction.
Figure 29:
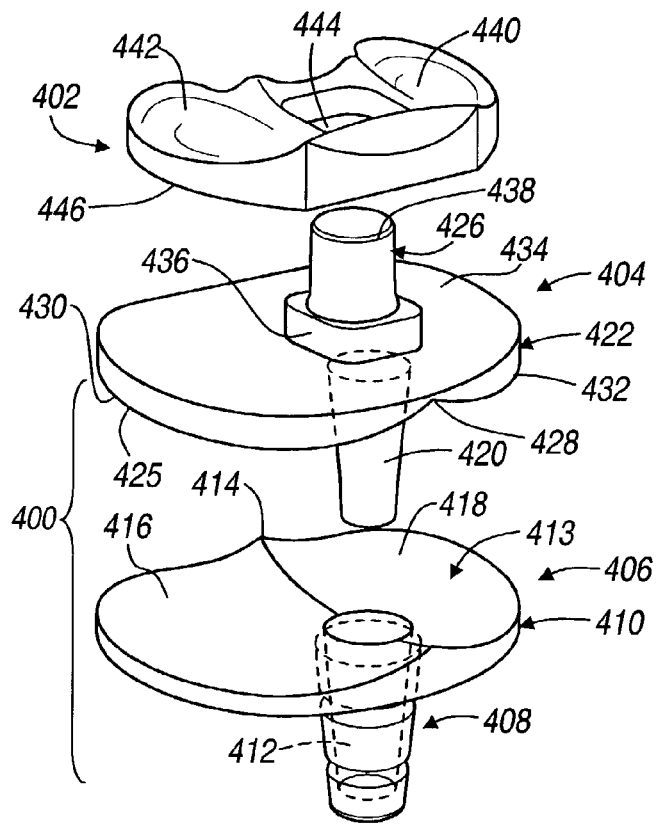
FIG. 29 is an exploded perspective view of a tibial component of a knee prosthetic according to an alternative embodiment.
Figure 30:
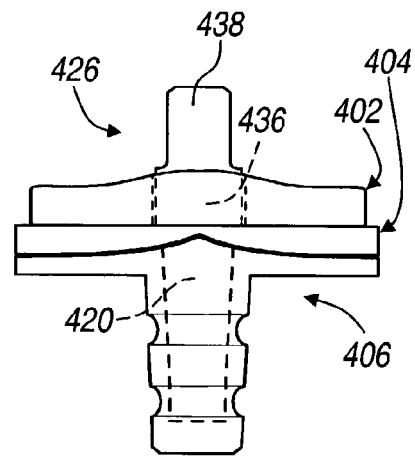
FIG. 30 is a front elevational view of the tibial component illustrated in FIG. 29.

In this embodiment when the knee is substantially unrotated, as illustrated in FIGS. 27 and 27a, the femoral component 352 may include varus and valgus distraction, such that while one of the condylar portions 358 or 360 remain in substantial contact with its respective bearing surface 370 or 372, the other rides up along the bearing surface. The femoral component 352 is able to tilt relative to the tibial tray 376. With particular reference to FIG. 27, when the femoral component 352 is not rotated relative the tibial component 356, that is, the anterior/posterior axis A of the femoral component 352 is substantially parallel to the anterior/posterior axis B of the PS post 366, substantially no portion of the superior portion 384 of the PS post 366 is touching or engaging a portion of the box 364. In this orientation, the femoral component may substantially include various varus or valgus distraction X, generally only limited by the soft tissue to between about 0° and about 20°, relative to the tibial component 356. As illustrated in FIG. 27a when the femoral component 352 is not rotated, that is rotated approximately 0°, the femoral component 352 can distract relative the tibial component 356. Generally, the femoral component 352 can distract at least about 20° when in this unrotated position. It will be understood, however, that different designs of the superior portion 384 of the PS post 366 can limit or increase the amount of distraction allowed the femoral component 352. Moreover, when the post 366 is modular, different PS posts may have different sizes or shapes to allow more or less distraction of differing degrees of rotation.

Figure 28:
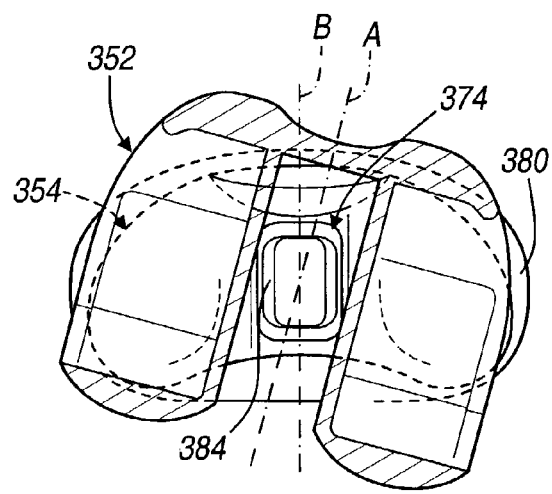
FIG. 28 is a partial cross-sectional elevational view of the knee prosthetic of FIG. 26 in a rotated position.

With reference to FIG. 28, nevertheless, when the femoral component 352 is rotated relative the tibial component 356, the superior portion 384 of the PS post 366 engages the box 364. Generally, the superior portion 384 of the PS post 366 is shaped so that the superior portion 384 of the PS post 366 engages the box 364 at a predetermined rotational degree. When the superior portion 384 of the PS post 366 engages the box 364, the amount of varus or valgus distraction is substantially limited or eliminated. Therefore, when the femoral component 352 is rotated relative the tibial component 356, the femoral component 352 is more stabilized in the varus or valgus distraction positions. Varus and valgus distraction of the femoral component 352 can be limited or eliminated depending upon the amount of rotation of the femoral component 352 relative the tibial component 356. When the femoral component is rotated between about plus or minus 10° to about 15°, the varus and valgus distraction Y of the femoral component 352 is substantially limited. Such that when the femoral component 352 is rotated to about 15°, the varus and valgus distraction is only about between 0° and about 5°. Generally, the varus and valgus distraction may also be substantially eliminated when the femoral component 352 is rotated far enough. The rotational position determines or limits the distraction depending upon the knees implanted in the particular patient. It will be understood that varying the size of the superior portion 384 of the PS post 366 varies the amount of rotation required to limit varus or valgus distraction.

It will be further understood that although a generally pyramidal or conical shape of the superior portion 384 is illustrated other appropriate shapes may be used. Other shapes include tapering rectangles or triangular pyramids. Alternatively, the PS guide post 206, shown above in FIG. 15 and described, may also provide an appropriate shape. The shapes, at one rotational displacement, allows the femoral component 352 to distract varus or valgus from the tibial component 356, while at another rotational displacement, the femoral component 352 is not able to distract or distracts to a lesser extent.

Referring to FIGS. 29–32, an eighth embodiment of a portion of a PS knee prosthesis is illustrated. The PS knee prosthesis generally includes a tibial component 400 and a bearing member or component 402. The tibial component 400 includes a tibial bearing component 404, which operatively interconnects with a tibial connector 406. The tibial connector 406 includes a tibial stem 408, a tibial connecting component tray 410, and a tibial connecting component bore 412, which extends through the tibial stem 408 and through the tibial connecting component tray 410. A superior surface 413 of the tibial connecting tray 410 defines a generally bi-helical surface, which includes a raised middle portion 414, a first depression 416, and a second depression 418, wherein the depressions are formed on either side of the raised portion 414.

The tibial bearing component 404 includes a supplementary tibial stem 420, that extends inferiorly from a tibial bearing component tray 422. The tibial bearing component stem 420 forms a generally taper connection with the bore 412 of the tibial connecting member 406. Although the connection is taper in design, the supplementary tibial stem 420 is able to rotate and distract within the bore 412. Extending superiorly from the tibial bearing member tray 422 is a post 426. An inferior side 425 of the tibial bearing member tray 422 defines a surface, which substantially mates with the superior surface 413 of the tibial connecting member 406. A superior depression 428, extends the anterior to posterior length of the tibial bearing member tray 422, although obstructed by the post 420. On a first side of the superior compression 428 is a first lobe 430, which extends inferiorly from the tray 422 and on a second side, a second lobe 432, which also extends inferiorly from the tray 422. Therefore, the inferior surface 425 of the tray 422 substantially mates or nests with the superior surface 413 of the tibial connecting member 406.

The tray 422 also defines a bearing articulation surface 434 on its superior side. The articulating surface 434 is substantially polished, such that the bearing component 402 may articulate smoothly on the surface 434. The post 426 includes an inferior portion 436 substantially closer to the articulating surface 434 than a superior portion 438 of the post 426. The inferior portion 436 is illustrated to have a substantially square outer perimeter. As described more fully herein, however, the perimeter of the inferior portion 436 may have any appropriate perimeter, such that it can, in at least one orientation, lock with the bearing component 402. The superior portion 438 of the post 426 is adapted to substantially mate with a cam formed in an appropriate femoral component (not illustrated here), an such as described above.

The bearing component 402 generally includes a first bearing portion 440 and a second bearing portion 442, which would substantially mate with an appropriate femoral component, described above, but not illustrated here. Formed between the first and second bearing portions 440, 442 is a bearing opening 444. The bearing opening 444 extends through the bearing component 402 allowing for the post 426 to extend through the bearing opening 444. An inferior surface of the bearing component 402 defines a tibial bearing surface 446. The tibial bearing surface 446 of the bearing component 402 is able to articulate on the surface 434 of the tibial bearing component 404.

The opening 444 has a dimension in at least one direction, which substantially mates with the inferior portion 436 of the post 426. For example, and illustrated here, the inferior portion 436 is substantially square in perimeter and the opening 444 has a medial lateral distance, which is substantially equal to the length of a side of the inferior portion 436. Therefore, when the bearing component 402 is resting on the surface 434, the bearing component 402 may not substantially move medially or laterally relative to the tibial bearing component 404. Nevertheless, the anterior to posterior length of the opening 444 is greater than the length of the anterior posterior side of the inferior portion 436 of the post 426. The greater dimension allows the bearing component 402, while resting on the surface 434, to move anteriorly and posteriorly. One consequence of the bearing opening 444 having a medial to lateral width substantially equal to the medial to lateral width of the posterior component 436 is that the bearing component 402 may not twist or rotate relative the tibial bearing component 404. Therefore, the bearing component 402 only has one degree of freedom, that being anteriorly and posteriorly, relative the tibial bearing component 404.

Figure 31:
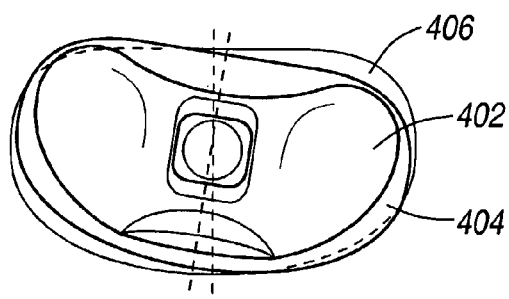
FIG. 31 is top elevational view of a knee prosthetic illustrated in FIG. 29 where a superior portion is rotated relative to an inferior portion.
Figure 32:
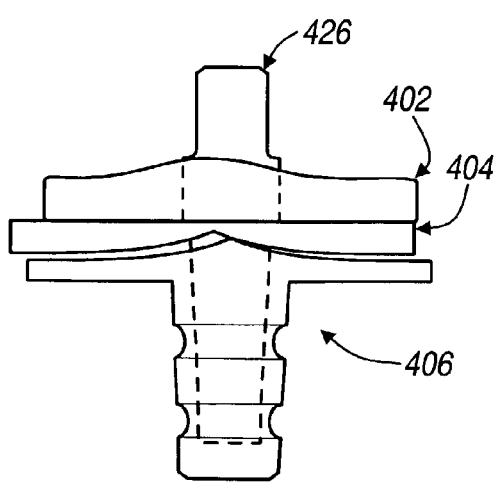
FIG. 32 is a front elevational view of the tibial component illustrated in FIG. 31.

Although the bearing component 402 does not rotate relative the tibial bearing component 404, the tibial bearing component 404 is able to rotate relative the tibial connecting portion 406. With particular reference to FIGS. 31 and 32, when the prosthesis is rotated, the bearing component 402 and the tibial bearing component 404 rotate substantially as one member. As this occurs, the inferior surface 425 of the tray 422 rides along the superior surface 413 of the tibial connecting portion 406. Due to the mating helical portions, the rotation causes a distraction of the tibial bearing component 404 from the tibial connecting component 406. The amount of distraction depends upon the size of the first or second lobes 430 or 432 or the raised ridge 414. The greater the size, the greater the distraction.

As the tibial bearing component 404 becomes distracted from the tibial connecting portion 406, the soft tissue, such as the medial and lateral collateral ligaments which remain in the knee after the knee replacement, tightens. This, in turn, allows for the knee to remain stable even when the portions are rotating relative one another. This allows a knee prosthesis, including the tibial component 400 and the bearing component 402, to include less constraints to support the knee in these inferior portion 436 of the post 426 in only one direction, the bearing component 402 may still articulate anteriorly and posteriorly on the surface 434.

In one alternative of the eighth embodiment, the tibial bearing component 404 is formed of a substantially rigid or hard material, such as cobalt chromium alloys, or titanium, or other appropriate biologically compatible metals. While the tibial connecting component 406 and the bearing component 402 are formed of a suitable, more flexible material, such as ultra high molecular weight polyethylene. The tibial connecting component 406, including the bore 412, is reinforced by the supplementary tibial post 420 of the tibial bearing component 404. Therefore, although the tibial connecting component 406 is formed of a polyethylene material, the supplementary tibial post 420, formed of an appropriate rigid material, reinforces the tibial post 408. It will be understood that other appropriate materials may also be used to form the appropriate parts. In addition, although a helical surface is disclosed, other appropriate surfaces may be used to form distracting surfaces wherein the tibial bearing component 404 distracts when it is rotated relative the tibial connecting component 406.

Because the bearing component 402 may move anteriorly and posteriorly relative to the tibial bearing component 404, rollback may be achieved. In addition this allows congruent rollback and contact between the femoral component and the bearing component. Therefore, not only is rollback achieved, but a continuous and congruent contact is allowed by the inclusion of a distinct tibial bearing component 404. As the soft tissue is tightened, due to the distraction of the tibial bearing component 404 from the tibial connecting component 406, the knee, into which the portions are implanted, produces rollback. This again reduces the need for other constraints otherwise necessary to be formed into the knee prosthesis when not using the tibial component 400 and the bearing component 402.

Figure 33:
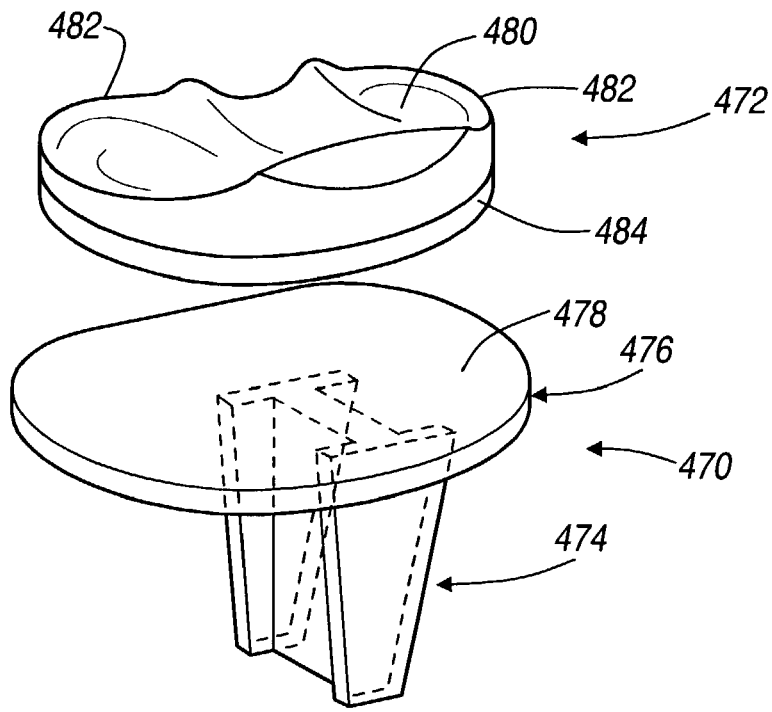
FIG. 33 is an exploded perspective view of a tibial component according to an alternative embodiment.
Figure 34:
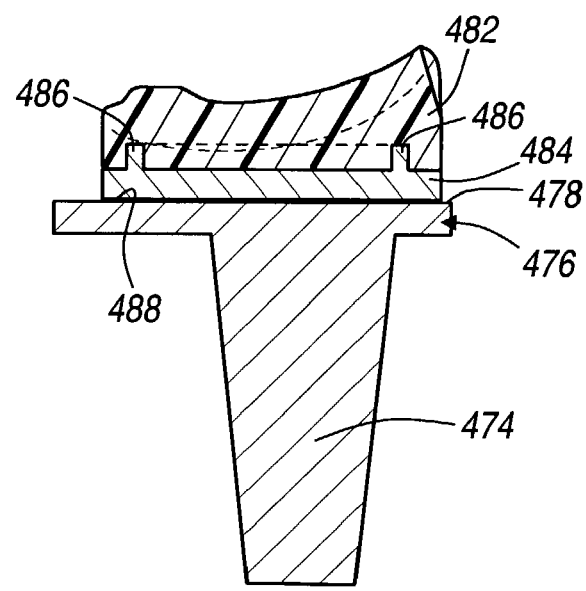
FIG. 34 is a partial sectional view of the alternative embodiment illustrated in FIG. 33.

With reference to FIGS. 33 and 34, a ninth embodiment of a tibial component 470 and an associated bearing component 472 is illustrated for a knee prosthesis of the present invention. Although a cruciate retaining tibial component 470 and bearing component 472 are illustrated, it will be understood that the following embodiment may also be used with a posterior stabilized knee prosthesis or other appropriate knee requiring a bearing component as disclosed herein, that may articulate with a tibial component. A post may be included on the tibial component 470 where the post is either modular or formed integrally with the tibial component 470. An opening may then be formed in the bearing component 472 to allow a floating bearing with a PS post.

The tibial component 470 generally includes a tibial stem 474 and a tibial tray 476. The superior side of the tibial tray 476 defines a tibial tray bearing surface 478. The tibial component 470 is generally formed of an appropriate biocompatible metal, such as cobalt chromium alloys or titanium. Therefore, the articulating surface 478 may be substantially highly polished to allow for a smooth articulation of the bearing component 472.

The bearing component 472 generally includes a first condylar bearing portion 480 and a second condylar bearing portion 482. In a knee prosthesis, the first and second condylar bearing portions 480 and 482 generally bear the condylar portions of the femoral component or of a natural femur. The bearing component 472 also includes a superior portion 482, which is formed of an appropriate bearing material. Bearing material examples may include polyethylene or other appropriate bearing materials. The superior portion 482 is molded to a hard posterior portion or base 484. The base 484 may be formed of appropriate hard material, for example, cobalt chromium alloys, ceramic, etc. In addition, the exterior surface of the base 484 may be augmented with other materials to increase the hardness of the exterior surface. For example, the exterior surface may be oxidized to form a hard ceramic thereon or may include a diamond coating to increase the hardness of the exterior surface of the base 484. Alternatively, the base 484 may be untreated or unaugmented.

With particular reference to FIG. 34, the base 484 includes the superior portion 482 molded thereto. To help stabilize the superior portion 482 onto the base 484, a flange 486 may be included on the base 484. The flange 486 may extend around the entire perimeter of the base 484 and spaced a distance from the exterior perimeter. Therefore, the material of the superior portion 482 may be molded over the flange 486 and extended to the external perimeter of the base 484. The flange 486 allows the material of the superior portion 482 to be substantially held or locked onto the base component 484. This assists during stresses after implantation into a body when the bearing component 472 articulates on the tibial articulation surface 478. When this occurs, the flange 486 stabilizes the superior portion 482 relative the base 484. It will be understood that a non-continuous flange may be used such as tabs or blocks formed on the superior side of the base 484 or roughened surfaces, ridges, grooves, etc.

The inferior surface 488 of the base 484 may also be highly polished to increase ease of articulation between the inferior surface 488 and the tibial tray bearing surface 478.

This allows a metal-on-metal bearing surface between the bearing component 472 and the tibial component 470 while enabling polyethylene articulation with the femoral component. Although metal-on-metal is particularly illustrated here, it will be understood that other appropriate articulating surfaces may be included. For example, the superior portion 482, including a polyethylene, can be molded onto an appropriate ceramic, which may form the base 484. The ceramic may be hardened to articulate with the tibial articulating surface 478.

Figures 35, 36:
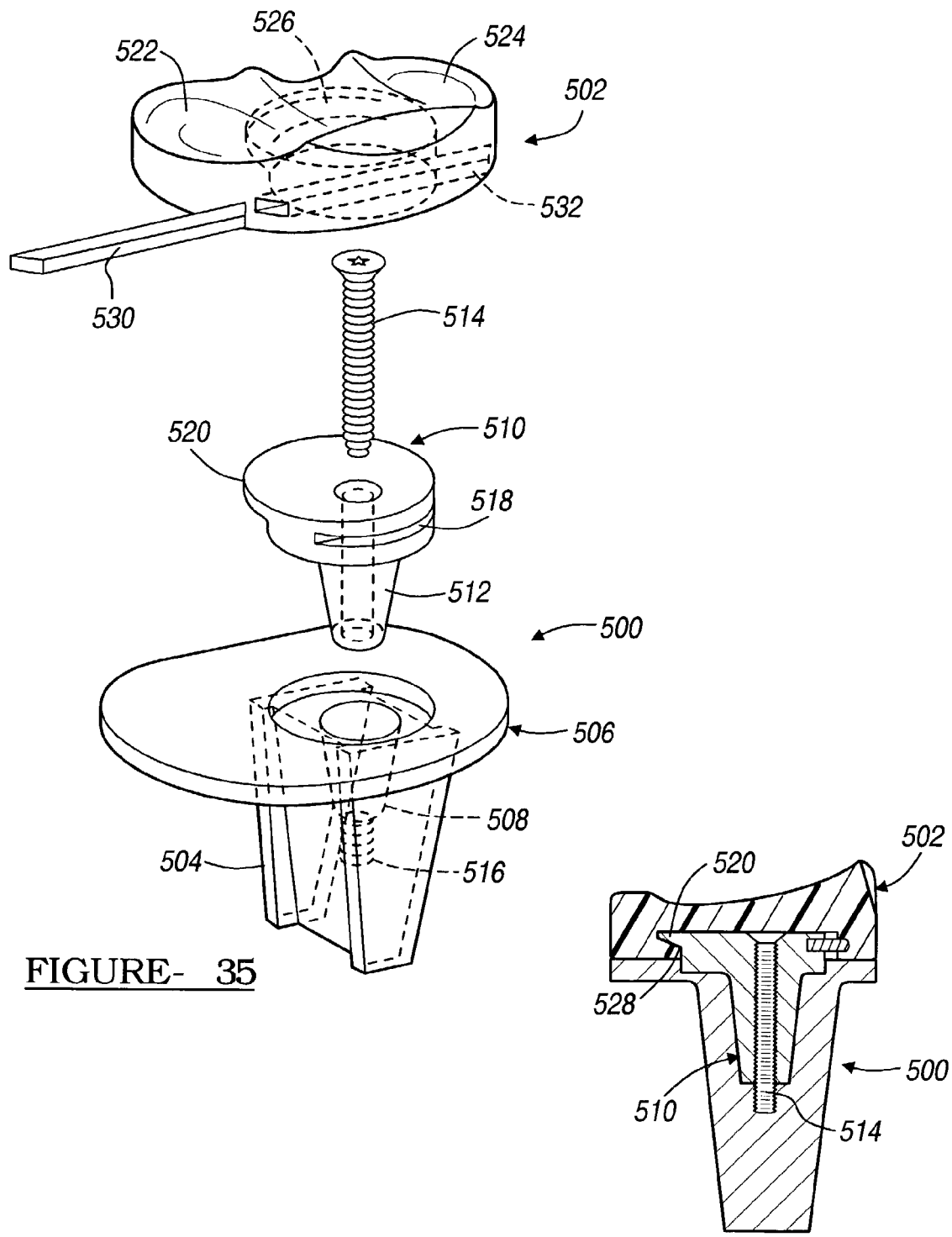
FIG. 35 is an exploded perspective view of a modular locked bearing tibial component according to an alternative embodiment.
FIG. 36 is a cross-sectional view of the tibial component illustrated in FIG. 35.

With reference to FIGS. 35–36, a tenth embodiment of a tibial component 500 and a bearing member 502 of a convertible knee prosthesis are illustrated for use with the present invention. Generally, the bearing component 502 may be locked or fixed relative to the tibial component 500 according to this embodiment, with a locking component 510. The tibial component 500 may be substantially similar to the modular tibial components illustrated and discussed above as shown in FIG. 15. In this way, the tibial component 500 may be used with a plurality of embodiments as discussed herein, and may also be used in the present embodiment to form a locked or fixed bearing knee prosthetic. This allows a reduction of possible components while not reducing, and actually increasing, the options of a surgeon implanting the knee prosthesis. For example, the bearing component 502 may include a post formed integrally therewith to form a PS knee with a fixed bearing. In addition, a cruciate retaining knee may be formed when the locking component 510 includes a post which extends above the bearing component 502.

The tibial component 500 includes a tibial stem 504, which extends inferiorly from a tibial tray 506. Formed in the stem 504 and extending through the tibial tray 506 is a tibial bore 508. The tibial bore 508 is adapted to receive the locking component 510, which includes a post 512, that is adapted to be received in the bore 508, via a Morse taper connection. Additionally, a screw or other member 514 may be placed through the locking member 510 to engage an internal thread 516 in the tibial stem 504. The locking member 510 is oblong and includes a first locking portion or slot 518 and a second locking portion or edge 520.

The bearing component 502, on a superior side, includes a first and second condylar bearing portion 522 and 524. Although the bearing component 502 may be formed of any appropriate material, the bearing component 502 is generally formed of an ultra high molecular weight polyethylene. The bearing component 502 also defines a locking recess 526. The locking recess 526 generally mates with the locking member 510. It will be understood that although a particular embodiment is illustrated here, other appropriate shapes may be formed, in the bearing component 502, such that the locking recess 526 will mate with an appropriately formed locking member 510.

The locking recess 526 includes a mating lip or ledge 528, which engages or mates with the locking ledge 520 on the locking component 510. The material of the bearing component 502 is generally slightly flexible, such that it may be deformed under enough stress. The locking lip 528 may be engaged under the locking ledge 520 and the bearing component 502 may then snap or be flexed to engage the locking member 510. In this way, the superior portion of the locking member 510 is substantially received in the locking recess 526 of the bearing component 502. After this, a locking bar 530 engages a locking bore 532, formed in the bearing component 502, and the locking slot 518 of the locking member 510. Therefore, the locking bar 530 interlocks the locking member 510 and the bearing component 502. Once the locking bar 530 is, transversely inserted, the bearing component 502 is held relative the tibial component 500.

This substantially modular configuration of forming a lock or locking bearing component 502 allows for more variation and options during the implant procedure. The tibial component 500 may be used for floating bearing knee prosthesis where the post extending from the tibial component is modular and is secured within bore 508. Alternatively, the same tibial component 500 may be used and once the implant procedure has begun, the physician may determine that a floating bearing posterior stabilized knee is not needed, however, a PS knee prosthesis with a fixed bearing is desired. This also allows revision of a previously implanted knee prosthesis from a floating bearing to a fixed bearing without replacing a well fixed tibial component. Rather than providing a entirely separate fixed bearing component, this embodiment will allow a locking member 510 and an appropriate bearing component 502 to form a fixed bearing knee prosthesis.

Figure 37:
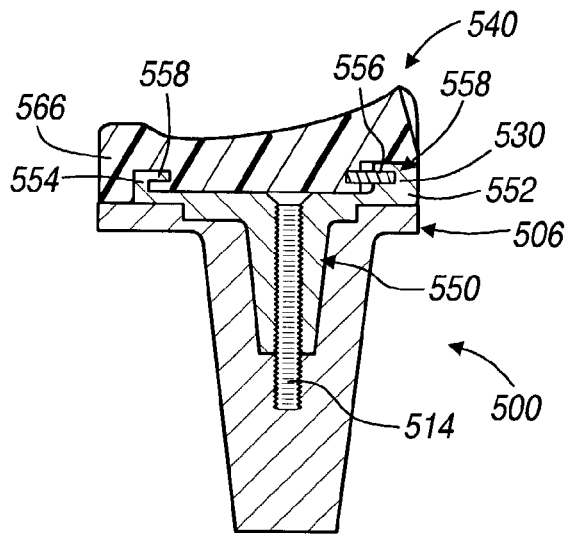
FIG. 37 is an alternative embodiment of the modular locking bearing component illustrated in FIG. 36.
Figure 38:
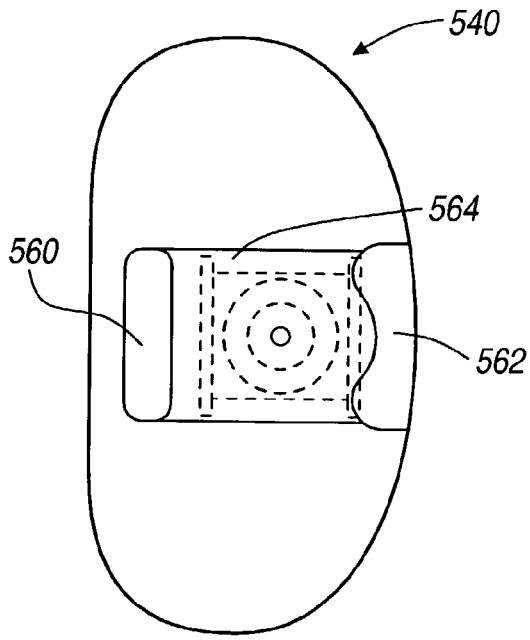
FIG. 38 is a diagrammatic elevational view of the locking bearing portion of the locking bearing tibial component.

With reference to FIGS. 37 and 38, an alternative embodiment of the tenth embodiment of the knee prosthesis including a modular tibial component allowing for a locked bearing is illustrated, which includes the tibial component 500 and a bearing component 540, which may be used in a knee prosthesis requiring a locked or fixed bearing. Like reference numerals refer to like elements as discussed in the above embodiments illustrated in FIGS. 35 and 36. In this embodiment, a locking component 550 is held into the tibial component 500 with a Morse Taper and the screw 514. The locking component 550 includes an anterior locking portion 552 and a posterior locking portion 554. The anterior locking portion 552 includes a slot 556, while the posterior locking portion 554 includes an anteriorally extending finger 558. The slot 556 on the anterior locking portion 552 receives the locking bar 530 after the bearing component 540 has been seated in place.

The bearing component 540 includes a posterior cut out or recess 560 to receive the posterior locking portion 554. The bearing component 540 also includes an anterior cut out or recess 562 to receive the anterior locking portion of 552. Additionally, the bearing component 540 includes an anterior to posterior recess or channel 564 to receive the superior extending portion of the locking component 550. Therefore, the bearing 540 includes several recesses or cut outs formed into the bearing such that it will fit properly onto the tibial tray 506. Moreover, the bearing component 540 includes a posterior portion 566 which extends onto the tibial tray 506 posteriorly of the posterior locking member 554.

Figure 39:
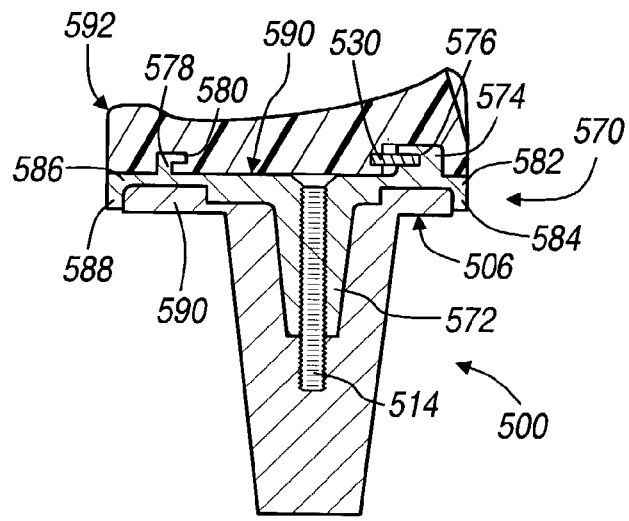
FIG. 39 is a cross-sectional view of alternative modular locking bearing components as illustrated in FIG. 36.

With reference to FIG. 39, a third alternative embodiment of the tenth embodiment of the knee prosthesis including the modular locking bearing tibial component 570 is illustrated, wherein like reference numerals reference like portions from the previous embodiments. In this embodiment, the locking member 572 includes an anterior locking portion 574 which includes a slot 576 to receive the locking bar 530. Also formed on the locking component 572 is a posterior locking portion 578 which includes an anteriorly extending finger 580. The locking component 572 also includes an anteriorally extending tray portion 582 which may include an inferiorly extending finger 584. Also included on the tray portion of the locking component 572 is a posteriorly extending tray portion 586 which also includes an inferiorly extending finger 588. Therefore, the locking component 572 includes an upper or tray portion 590 which substantially surrounds the tibial tray 506 to provide further support, strength and rigidity.

The tray portion 590 may provide any appropriate thickness necessary to provide a required strength to the locking component 572. According to this embodiment, however, the bearing component 592 does not require any additional cut outs to accommodate the upper portion of the locking component 572. Particularly, the anterior to posterior recess of the embodiment illustrated in FIG. 38 is not required. Therefore, the bearing component 592, used in conjunction with the locking component 572, may be similar to other fixed bearings. This may assist in component choice and relieving inventory constraints by not requiring an additional and new bearing component.

Figure 40:
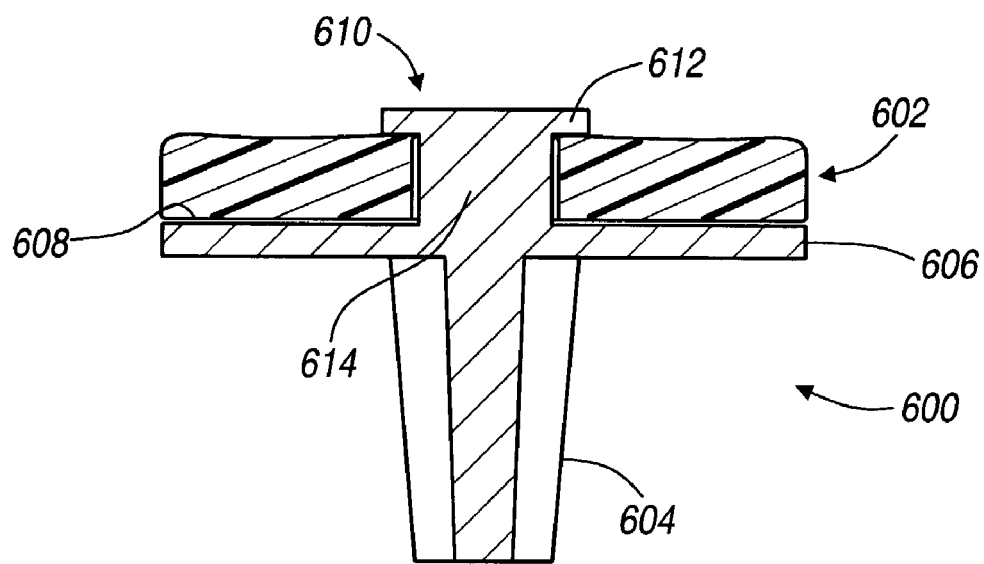
FIG. 40 is a cross-sectional view of a tibial component including a bearing component according to an alternative embodiment.
Figure 41:
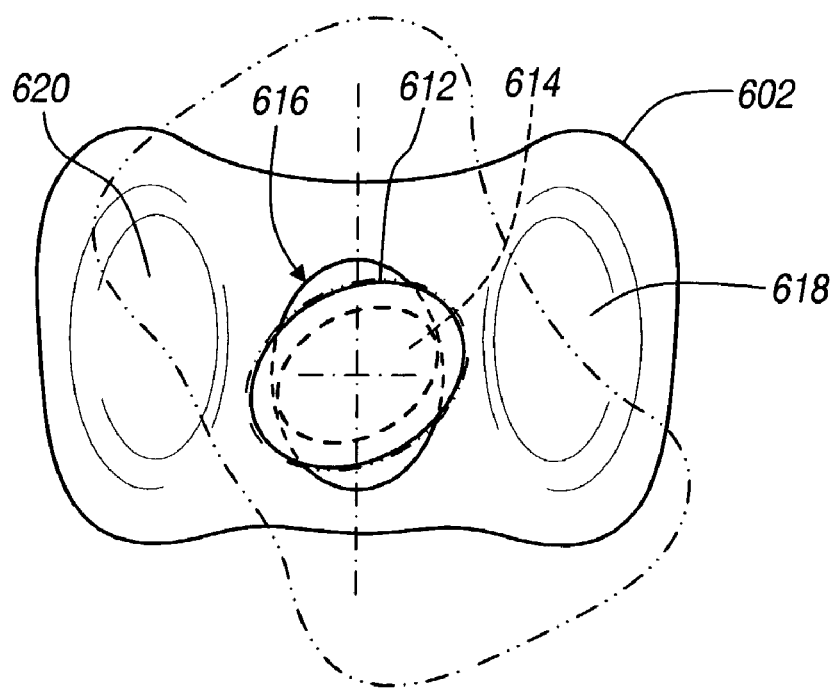
FIG. 41 is a superior elevational view of the tibial and bearing components of FIG. 41 illustrating the bearing component in an installed position.

With reference to FIGS. 40 and 41, an eleventh embodiment of a knee prosthetic may include a tibial component 600 and a bearing member or component 602. The tibial component 600 generally includes a tibial stem 604 and a tibial tray 606 which includes a tibial tray bearing surface 608. The tibial tray bearing surface 608 is where the bearing component 602 bears upon the tibial tray 606 and may articulate thereon. The tibial component 600 may also include a posterior (PS) stabilizing or cruciate retaining (CR) guide post 610 extending superiorly from the tibial tray bearing surface 608. The post 610 includes a superior or locking portion 612 and an inferior or cutout portion 614. The superior portion 612 of the post 610 includes a medial to lateral (M-L) dimension that is greater than its anterior to posterior (A-P) dimension. Thus, the superior portion 612 defines a generally oval or oblong shape. The inferior portion 614 also includes an M-L dimension which is greater than its A-P dimension, but is also smaller in each of those dimensions than the respective dimensions of the superior portion 612. Therefore, the inferior portion 614 defines a cutout or recess which the superior portion 612 overhangs.

The bearing component 602 includes the portions generally described above included in the bearing components, these generally include a bearing opening or hole 616. The bearing hole 616, defined by the bearing component 604, includes an A-P dimension which is greater than its M-L dimension. Therefore, the bearing opening 616, defined by the bearing component 602, includes a substantially oblong or oval shape aligned in the A-P direction. When the bearing component 602 is in the operable position, the medial and lateral edges of the superior portion 612 of the post 610 overhang a portion of the bearing component 604. The bearing component 602 also includes a first condylar bearing surface 618 and a second condylar bearing surface 620. Generally, the superior portion 612 will not impinge upon or extend over the first and second condylar bearing surfaces 618 and 620. Because the superior portion 612 overhangs a portion of the bearing component 602, the bearing component is held substantially adjacent the tibial bearing surface 608. Nevertheless, the bearing component 602 may rotate and articulate in an anterior to posterior direction and in a medial to lateral direction because of the bearing opening 616 is greater in all dimensions than the inferior portion 614 of the post 610. The superior portion 612 of the post 610 ensure that the bearing component 602 will not substantially leave its articulating position on the tibial tray bearing surface 608 during use. Substantially prevent rocking or tipping of the bearing relative to the tibial plate 606.

As illustrated in phantom lines in FIG. 41, the bearing component 604 may be implanted over the superior portion 612 of the post 610 by rotating the bearing component 602 such that the A-P dimensions of the bearing hole 616 match with the angled M-L dimension of the superior portion 612 and the M-L dimensions of the bearing hole 616 match with the angled A-P dimensions of the superior portion 612, or that the bearing hole 616 is greater than each of the dimensions of the superior portion 612, such that the bearing component 604 may fit over the superior portion 612 of the post 610. After fitting the bearing component 604 over the superior portion 612, the bearing component 602 may be rotated to its operational orientation. In the operational orientation, the dimensions of the bearing hole 616 interfere with the dimensions of the superior portion 612 such that the bearing component 604 is held substantially adjacent the tibial bearing surface 608.

The bearing hole 616 is substantially keyed to the superior portion 612 of the post 610. It will be understood that although an oval shape is illustrated here offset relative to the A-P axis, other appropriate shapes and axes may be used to form the keyed relationship. Where a first or non-operative position of the bearing component 602, relative the tibial component 600 allows for removal of the bearing component 602, relative the tibial component 600, but an operative orientation of the bearing component 602 relative the tibial component 600 does not allow the bearing component 602 to substantially distract from the tibial tray bearing surface 608. It will also be understood that the inferior portion 614 of the post 610 may have a height which is greater than the height of the bearing component 602 to allow distraction in a superior direction relative the tibial tray bearing surface 608, yet still engage the superior portion 612 of the post 610 before dislocating from the post 610.

Figure 42:
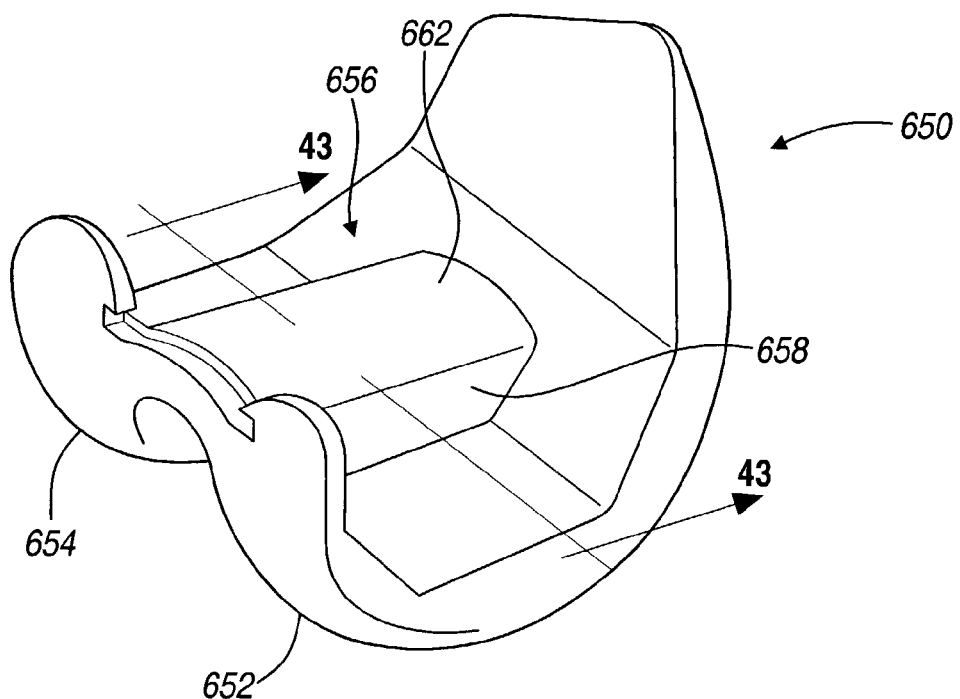
FIG. 42 is a perspective view of a femoral component according to an alternative embodiment.
Figure 43:
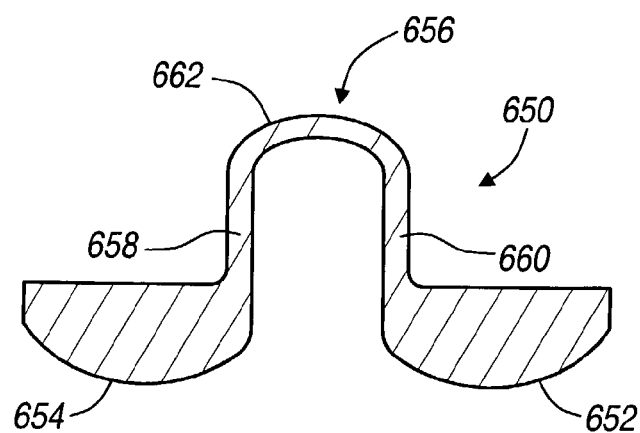
FIG. 43 is a cross-sectional view of the femoral component taken along line 43—43 of FIG. 42.

With reference to FIGS. 42 and 43, a femoral component 650 according to an alternative embodiment is shown. The femoral component 650 generally includes a first condylar portion 652 and a second condylar portion 654 each defining a condylar bearing surface that may articulate with an appropriate bearing component, as described above. Positioned between the first and second condylar portions 652 and 654 is an inter-condylar box 656. The inter-condylar box 656 includes a first sidewall 658 and a second sidewall 660. Interconnecting the two sidewalls 658 and 660 is a top wall or arch 662. The top wall 662 includes a radius of curvature such that it is not substantially planar or flat across its width. In addition, the edge or interconnection between the first wall 658 and the top 662 includes a radius, as does the interconnection between the second wall 660 and the top 662. Therefore, the superior portion of the box 662 is substantially defined by a radius which has a center of curvature inferior of the top 662 of the box 656.

Generally, a femur is prepared to accept the femoral component 650 by first removing the distal end of the femur and then reaming and chiseling a portion of the femur to accept the box 656. When the top 662 of the box 656 includes a radius, the chiseling and reaming is substantially reduced and lessened when compared to the preparation necessary for a box that is substantially square or has sharper angles at the corners of the box. Therefore, the box 656 with the radius top 662 can decrease the amount of surgical time required to prepare the femur for implantation of the femoral component 650. In addition, it reduces the amount of bone that must be removed to accept the femoral component 650. Moreover, by removing a smaller portion of bone in the resection of the femur there is more bone over which the load, especially a side load, may be distributed. In addition, the rounded resection does not create stress corners which concentrate stress when a side load is applied to the femur. Nevertheless, the interior of the box 656 still provides a cam portion to accept a PS post which extends from an appropriate tibial component.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A prosthesis for replacing a knee joint between a femur and a tibia, the prosthesis comprising:
    a femoral component including a first condylar portion and a second condylar portion;
    an inter-condylar box, including a first side wall spaced apart from a second side wall, disposed between said first condylar portion and said second condylar portion;
    a tibial component, adapted to be implanted into the tibia; and
    a guide post extending superiorly from said tibial component, wherein said guide post includes a sagittal plane dimension or a coronal plane dimension;
    wherein said guide post is adapted to extend into said inter-condylar box when the prosthesis is implanted in the knee joint;
    wherein said femoral component is adapted to rotate about said guidepost between a first position and a second position;
    wherein a varus distraction or a valgus distraction is limited a first amount when said femoral component is in said first position and the varus distraction or the valgus distraction is limited a second amount when said femoral component is in said second position.

2. The prosthesis of claim 1, wherein said guide post operably engages said first side wall or said second side wall when said femoral component is in said second position.

3. The prosthesis of claim 2, wherein when said guide post operably engages said first side wall or said second side wall said femoral component is substantially limited as to the amount of varus distraction or valgus distraction.

4. The prosthesis of claim 1, wherein said inter-condylar box further includes:
    a top wall that includes a dimension spanning between said first side wall and said second side wall;
    wherein said spanning dimension of said top wall is less than a median plane dimension of said first side wall or said second side wall.

5. The prosthesis of claim 1, wherein said sagittal plane dimension is greater than said coronal plane dimension.

6. The prosthesis of claim 1, wherein said guide post is formed of a bio-compatible polymer.

7. The prosthesis of claim 4, wherein said median plane dimension is at least the distance between said first side wall and said second side wall.

8. The prosthesis of claim 1, wherein said guide post includes a tapered superior portion.

9. A prosthesis for replacing a knee joint between a femur and a tibia, the prosthesis comprising:
    a femoral component including a first condylar portion and a second condylar portion;
    an inter-condylar box, including a first side wall spaced apart from a second side wall, disposed between said first condylar portion and said second condylar portion;
    a tibial component, adapted to be implanted into the tibia; and
    a guide post extending superiorly from said tibial component, wherein said guide post includes a sagittal plane dimension or a coronal plane dimension;
    wherein said guide post is adapted to extend into said inter-condylar box when the prosthesis is implanted in the knee joint;
    wherein said femoral component is adapted to rotate about said guidepost between a first position and a second position;
    wherein a varus distraction or valgus distraction is limited when said femoral component is in said second position;
    wherein said guide post is selectively attachable to said tibial component, wherein said guide post is selected to determine the amount of varus or valgus distraction of the prosthesis.

10. A prosthesis for replacing a knee joint between a femur and a tibia, the prosthesis comprising:
    a femoral component including a first condylar portion and a second condylar portion;
    an inter-condylar box, including a first side wall spaced apart from a second side wall, disposed between said first condylar portion and said second condylar portion;
    a tibial component, adapted to be implanted into the tibia; and
    a guide post extending superiorly from said tibial component, wherein said guide post includes a sagittal plane dimension or a coronal plane;
    wherein said guide post is adapted to extend into said inter-condylar box when the prosthesis is implanted in the knee joint;
    wherein said femoral component is adapted to rotate about said guidepost between a first position and a second position;
    wherein a varus distraction or valgus distraction is limited when said femoral component is in said second position;
    wherein said guide post is selectively attachable to said tibial component, wherein said guide post is selected to determine when said second position is reached by said femoral component.

11. A prosthesis for replacement of a knee joint between a femur and a tibia, the prosthesis comprising:
    a femoral component including:
        a first condylar portion and a second condylar portion spaced apart;
        an inter-condylar box, defined between said first condylar portion and said second condylar portion, including a first side wall extending superiorly said first condylar portion and a second side wall extending superiorly of said second condylar portion;
    a guide post operable to engage said inter-condylar box;
    wherein said femoral component is adapted to be positioned between an engaged and a non-engaged position with said guide post such that when said femoral component is in said engaged position with said guide post said femoral component has substantially limited varus distraction or valgus distraction;
    a bearing component including a bearing portion and an articulating portion, adapted to articulate on said tibial component;
    wherein said bearing portion is formed of a first material and said articulating portion is formed of a second material.

12. A prosthesis for replacing a knee joint between a femur and a tibia, the prosthesis comprising:
    a femoral component including a first condylar portion and a second condylar portion;
    an inter-condylar box, including a first side wall spaced apart from a second side wall, disposed between said first condylar portion and said second condylar portion;
    a tibial component, adapted to be implanted into the tibia; and a guide post extending superiorly from said tibial component including a taper at a superior end;

wherein said guide post is adapted to extend into said inter-condylar box when the prosthesis is implanted in the knee joint;

wherein said femoral component is adapted to rotate about said guide post between a first position and a second position;

wherein a varus distraction or valgus distraction is limited when said femoral component is in said second position;

wherein said guide post is selectively attachable to said tibial component, wherein said guide post is selected to determine the amount of varus or valgus distraction of the prosthesis.

13. A prosthesis for replacing a knee joint between a femur and a tibia, the prosthesis comprising:

a femoral component including a first condylar portion and a second condylar portion;

an inter-condylar box, including a first side wall spaced apart from a second side wall, disposed between said first condylar portion and said second condylar portion;

a tibial component, adapted to be implanted into the tibia; and a guide post extending superiorly from said tibial component including a taper at a superior end;

wherein said guide post is adapted to extend into said inter-condylar box when the prosthesis is implanted in the knee joint;

wherein said femoral component is adapted to rotate about said guide post between a first position and a second position;

wherein a varus distraction or valgus distraction is limited when said femoral component is in said second position;

wherein said guide post is selectively attachable to said tibial component, wherein said guide post is selected to determine when said second position is reached by said femoral component.

14. A prosthesis for replacing a knee joint between a femur and a tibia, the prosthesis comprising:

a femoral component including a first condylar portion and a second condylar portion;

an inter-condylar box, including a first side wall spaced apart from a second side wall, disposed between said first condylar portion and said second condylar portion;

a tibial component, adapted to be implanted into the tibia; and a guide post extending superiorly from said tibial component including a taper at a superior end;

wherein said guide post is adapted to extend into said inter-condylar box when the prosthesis is implanted in the knee joint;

wherein said femoral component is adapted to rotate about said guidepost between a first position and a second position;

wherein a varus distraction or valgus distraction is limited when said femoral component is in said second position;

wherein said superior end of said guide post engages said inter-condylar box at said second position.

* * * * *